US010545093B2

(12) United States Patent
Swager et al.

(10) Patent No.: US 10,545,093 B2
(45) Date of Patent: Jan. 28, 2020

(54) SELECTIVE DETECTION OF ALKENES OR ALKYNES

(71) Applicant: Massachusetts Institute of Technology, Cambridge, MA (US)

(72) Inventors: Timothy M. Swager, Newton, MA (US); Joseph M. Azzarelli, Cambridge, MA (US); Kathleen R. White, Dubuque, IA (US)

(73) Assignee: MASSACHUSETTS INSTITUTE OF TECHNOLOGY, Cambridge, MA (US)

( * ) Notice: Subject to any disclaimer, the term of this patent is extended or adjusted under 35 U.S.C. 154(b) by 303 days.

(21) Appl. No.: 14/246,008

(22) Filed: Apr. 4, 2014

(65) Prior Publication Data

US 2016/0169810 A1 Jun. 16, 2016

Related U.S. Application Data

(60) Provisional application No. 61/809,362, filed on Apr. 6, 2013.

(51) Int. Cl.
| *G01N 21/78* | (2006.01) |
| *G01N 21/76* | (2006.01) |
| *G01N 33/00* | (2006.01) |
| *G01N 31/00* | (2006.01) |
| *G01N 27/00* | (2006.01) |
| *G01N 21/00* | (2006.01) |
| *G01N 7/00* | (2006.01) |

(52) U.S. Cl.
CPC .................. *G01N 21/78* (2013.01)

(58) Field of Classification Search
CPC .......... G01N 7/00; G01N 21/00; G01N 27/00; G01N 31/00; G01N 33/00; G01N 21/76
USPC .... 422/83, 98, 50, 52, 400, 403, 85, 90, 91; 436/43, 164, 167, 169, 171, 172
See application file for complete search history.

(56) References Cited

U.S. PATENT DOCUMENTS

| 4,142,901 | A | * | 3/1979 | Holstead ................. C09B 29/08 430/592 |
| 5,208,152 | A | | 5/1993 | Hilvert et al. |
| 5,310,525 | A | * | 5/1994 | Churchouse et al. ........ 422/412 |
| 5,334,623 | A | | 8/1994 | Holland |
| 6,312,537 | B1 | * | 11/2001 | Hiskey .................... C06B 43/00 149/36 |
| 6,737,236 | B1 | * | 5/2004 | Pieken .................. C07C 271/22 424/193.1 |
| 8,236,949 | B2 | | 8/2012 | Fox et al. |
| 2006/0263502 | A1 | | 11/2006 | Horsham et al. |
| 2009/0023916 | A1 | | 1/2009 | Fox et al. |
| 2010/0112680 | A1 | * | 5/2010 | Brockwell et al. ........ 435/287.9 |
| 2010/0166604 | A1 | | 7/2010 | Lim et al. |
| 2013/0122516 | A1 | * | 5/2013 | Hong et al. .................... 435/7.1 |

(Continued)

OTHER PUBLICATIONS

International Search Report dated Aug. 18, 2014, issued in International Application No. PCT/US2014/033037.

(Continued)

*Primary Examiner* — Brian J. Sines
(74) *Attorney, Agent, or Firm* — Steptoe & Johnson LLP

(57) ABSTRACT

A detector can detect an analyte including a carbon-carbon multiple bond moiety and capable of undergoing Diels-Alder reaction with a heteroaromatic compound having an extrudable group. The detector can detect, differentiate, and quantify ethylene.

13 Claims, 18 Drawing Sheets

(56) References Cited

U.S. PATENT DOCUMENTS

| 2013/0189287 | A1* | 7/2013 | Bregeon | .......... A61K 47/48215 |
| | | | | 424/180.1 |
| 2013/0244975 | A1* | 9/2013 | Baldwin et al. | ................ 514/56 |
| 2014/0378538 | A1* | 12/2014 | Bancel | ........................ 514/44 R |
| 2015/0099277 | A1* | 4/2015 | Devaraj | ............... C07D 237/26 |
| | | | | 435/69.1 |

OTHER PUBLICATIONS

Written Opinion of the International Searching Authority dated Aug. 18, 2014, issued in International Application No. PCT/US2014/033037.
Notification of Transmittal of the International Search Report and the Written Opinion of the International Searching Authority, or The Declaration dated Aug. 18, 2014, issued in International Application No. PCT/US2014/033037.

\* cited by examiner (a)

(b)

SELECTIVE DETECTION OF ALKENES OR ALKYNES

PRIORITY CLAIM

This application claims priority to U.S. Provisional Patent Application No. 61/809,362, filed Apr. 6, 2013, which is incorporated by reference in its entirety.

STATEMENT OF GOVERNMENT SUPPORT

This invention was made with government support under Contract No. W911NF-07-D-0004 awarded by the Army Research Office. The government has certain rights in the invention.

TECHNICAL FIELD

This invention relates to detection methods and detectors for sensing alkenes or alkynes.

BACKGROUND

The detection and monitoring of alkene and alkyne is of great interest and importance. Current methods for alkene and alkyne detection, differentiation and quantitation are expensive and there is a growing need of a method that is low-cost and ease-of-use. Containing unsaturated functional groups, alkene and alkyne are capable of undergoing Diels-Alder type reactions.

SUMMARY

In one aspect, a detector for detecting an analyte can include a housing including a detection region comprising a compound having an extrudable group and capable of undergoing Diels-Alder reaction with the analyte including a carbon-carbon multiple bond moiety. The compound can be a heteroaromatic compound.

In certain embodiments, the detector can be a color based detector. In other embodiments, the detector can be a fluorescence based detector. In other embodiments, the detector can be a resistivity based detector.

In some embodiments, the analyte can include ethylene. In some embodiments, the heteroaromatic compound can include tetrazine. In some embodiments, the heteroaromatic compound can include bis-2-pyridyl-1,2,4,5-tetrazine.

In some embodiments, the heteroaromatic compound can selectively react with a sterically unencumbered alkene. In some embodiments, the heteroaromatic compound can selectively react with a sterically unencumbered alkyne.

In some embodiments, the detection region can include a colorimetric indicator that changes color after the Diels-Alder reaction. In some embodiments, the color based detector can include a copper salt, a nickel salt, a silver salt, a zinc salt, an aluminum salt, or a gold salt. In some embodiments, the detection region can include a machine readable pattern. In some embodiments, the color based detector can include a reader capable of reading the pattern.

In some embodiments, the detection region can include other materials that report on the state of the molecule, or collection of molecules, that undergo Diels-Alder reactions. For example, the detection region can include a material initially having low luminescence and after the Diels-Alder reaction with an analyte the composition will have an increased luminescence. In other examples, the detection region can include a material initially having high luminescence and after the Diels-Alder reaction with an analyte the composition will have reduced luminescence. Multiple materials with different luminescent properties can be used to provide for light emission and absorbance patterns that can be read. In these embodiments, the detection region can include a luminescent material. Examples of suitable luminescent materials can include one or more of a conjugated molecule, a conjugated polymer, or an inorganic phosphor.

In other embodiments, the detection region can include an electrically conductive material and the measured response can be a change in the resistivity in the detection region. In some cases, the Diels-Alder reaction with an analyte can increase the resistance in the detection region. In other cases, the Diels-Alder reaction with an analyte can decrease the resistance in the detection region. In these embodiments, the detection region can include one or more of a carbon nanotube, graphite, graphene, a semiconductor nanowire, a metal nanoparticle, a metal nanowire, or a conducting polymer.

In another aspect, a method of detecting an analyte in a sample including a carbon-carbon multiple bond moiety can comprising exposing a detection region of a detector including a compound having an extrudable group and capable of undergoing Diels-Alder reaction with the analyte including a carbon-carbon multiple bond moiety to the sample, and detecting a property change of a reaction mixture comprising the heteroaromatic compound based on the presence of the analyte in the sample. In some embodiments, the analyte can be ethylene.

In some embodiments, detecting the property change can include monitoring absorbance of the detection region. In some embodiments, detecting the property change can include monitoring fluorescence of the detection region. In some embodiments, detecting the property change can include monitoring conductivity of the detection region. In some embodiments, the method can further include determining a reaction rate constant of the analyte with the compound in the detection region of the detector. In some embodiments, the method can further include quantifying the amount of the analyte using the rate constant.

In some embodiments, the method can further include differentiating alkene classes, alkyne classes, or alkene and alkyne classes by correlating reactivity with initial and final colors of the reaction mixture.

In some embodiments, the method can further include quantifying the amount of the analyte using Red Green Blue color mapping. In some embodiments, the method can further include differentiating alkene classes, alkyne classes, or alkene and alkyne classes using Red Green Blue color space value. In some embodiments, the method can further include quantifying the amount of the analyte using Euclidean distance determined from the initial and final colors of the reaction mixture. In some embodiments, the method can further include differentiating alkene classes, alkyne classes, or alkene and alkyne classes using euclidean distance.

In some embodiments, the method can further include reading a machine-readable pattern in the detection region when the pattern appears. In some embodiments, the method can further include reading a machine-readable pattern in the detection region when the pattern vanishes.

In some embodiments, the reaction mixture can be in a solvent. In some embodiments, the solvent can include tetrahydrofuran, dichloromethane, acetonitrile, nitromethane, toluene, chloroform, propylene carbonate, dimethylsulfoxide, dimethylformamide or acetone. In some embodiments, the reaction mixture can be in solid formulation or solid substrate. In some embodiments, the reaction mixture can include a copper salt, a nickel salt, a silver salt, a zinc salt, an aluminum salt, or a gold salt.

In another aspect, a detector for detecting an analyte can include a housing including a detection region comprising a compound having electron donating or withdrawing character and capable of undergoing Diels-Alder reaction with the analyte including a carbon-carbon multiple bond moiety, and a conducting material that changes conductivity after the Diels-Alder reaction.

In certain embodiments, the compound can become less electron accepting after reacting with an alkene. The compound can become less electron donating after reacting with an alkene. Resistivity of the conducting material can change after the Diels-Alder reaction. The compound can selectively react with a sterically unencumbered alkene.

In certain embodiments, the detection region can include a colorimetric indicator that changes color after the Diels-Alder reaction. The detector can include a copper salt, a nickel salt, a silver salt, a zinc salt, an aluminum salt, or a gold salt. The detection region can include a machine readable pattern. The detector can include a reader capable of reading the pattern.

In certain embodiments, the detector can be a color based detector. The detector can be a fluorescence based detector. The detector can be resistivity based detector.

In certain embodiments, the detector can selectively detect an electron-poor alkene. The detector can selectively detect an electron-rich alkene. The selectivity for an electron-poor alkene can be with respect to an electron-rich alkene. The selectivity for an electron-rich alkene can be with respect to an electron-poor alkene.

In another aspect, a method of detecting an analyte in a sample including a carbon-carbon multiple bond moiety can include exposing a detection region of a detector including a compound having electron donating or withdrawing character and capable of undergoing Diels-Alder reaction with the analyte including a carbon-carbon multiple bond moiety, and detecting a property change of a conducting material after the Diels-Alder reaction based on the presence of the analyte in the sample.

Other aspects, embodiments, and features will be apparent from the following description, the drawings, and the claims.

BRIEF DESCRIPTION OF THE DRAWINGS

FIG. 13(B-1) and FIG. 13(B-2) shows photographs of the representations after exposure to $C_2H_4$ (1 atm) for 48 h.

DETAILED DESCRIPTION

Figure 1:
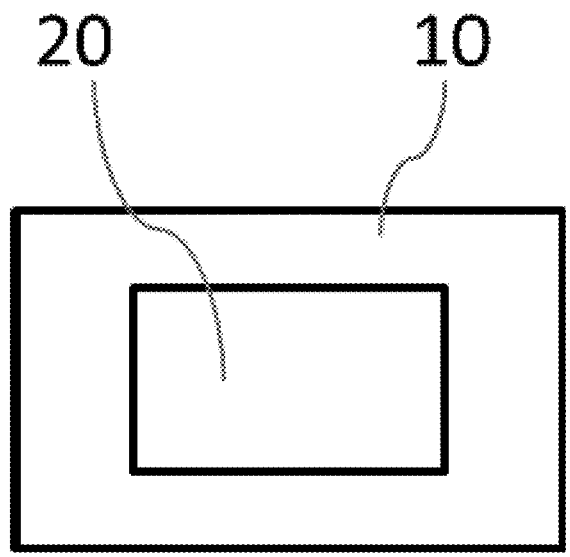
FIG. 1 is a block diagram showing one example of a detecting device.

Compounds containing unsaturated functional groups are capable of undergoing [4+2] cycloadditions (Diels-Alder type reactions), resulting in the loss of an extrudable group, such as dinitrogen. This structural change in the compound results in a change in its electronic properties of material including the compound, which are then transduced into various observable outputs, such as change in color, absorbance, fluorescence, or conductivity. These observable outputs allow for the determination of total amount of analyte exposure to device at various time points following initial exposure.

Diels-Alder Reaction

The Diels-Alder reaction is a cycloaddition reaction between a conjugated diene and a substituted alkene to form a substituted cyclohexene system. Some of the atoms in the newly formed ring do not have to be carbon. Some of the Diels-Alder reactions are reversible; the decomposition reaction of the cyclic system is then called the retro-Diels-Alder.

The simplest example is the reaction of 1,3-butadiene with ethene to form cyclohexene:

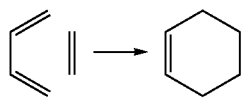

The analogous reaction of 1,3-butadiene with ethyne to form 1,4-cyclohexadiene is also known:

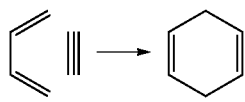

A heteroaromatic compound can be used for a Diels-Alder reaction. The heteroaromatic compound can have an extrudable group as shown in the following structure.

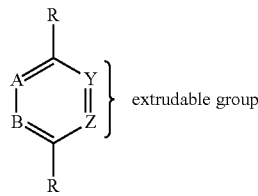

Each of A, B, Y and Z can be C—R, N, S, or O, such that Y and Z together form an extrudable group. Each R, independently, can be H, halo, alkyl, haloalkyl, or aryl.

An extrudable group is a group that leaves the heteroaromatic compound after the heteroaromatic compound undergoes a Diels-Alder reaction. One example of the extrudable group is di-nitrogen. Examples of compounds wherein di-nitrogen is extrudable group:

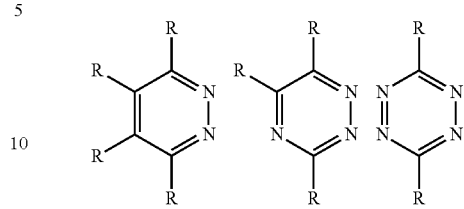

The following is a schematic representation of inverse-electron-demand hetero-Diels-Alder reaction of (1) with an unsaturated carbon-carbon bond to give (2) via transition state (T.S. 1) (2) spontaneously undergoes a retro-Diels-Alder reaction resulting in product (3) by extrusion of (4).

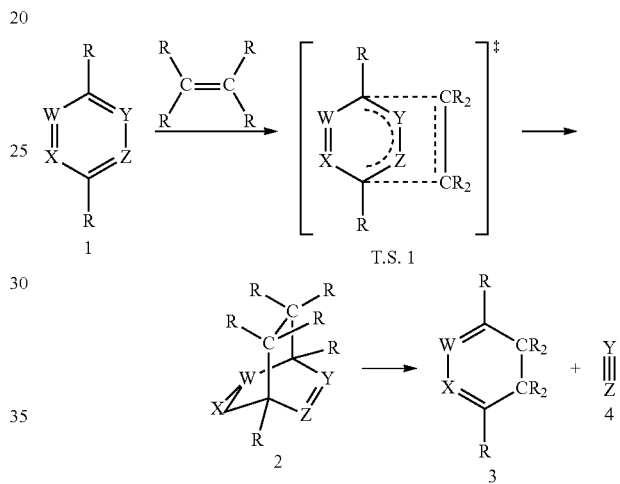

Table 1 and Table 2 show examples of tetrazines.

TABLE 1

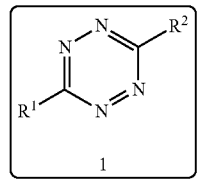

Symmetric Tetrazines

| entry | $R^1 = R^2$ | isolated yield | $\delta_{max}$ | $\epsilon(M^{-1}cm^{-1})$ | $k_2(M^{-1}s^{-1})$ |
|---|---|---|---|---|---|
| a | (2-pyridyl) | commercial | 538 | 415 | 19.41 |
| b | (3-pyridyl) | 26.4 | 540 | | very slow |

MeCN spans $\delta_{max}$, $\epsilon$, $k_2$ columns.

TABLE 1-continued

| entry | R | isolated yield | δ_max | ε(M⁻¹cm⁻¹) | k₂(M⁻¹s⁻¹) |
|---|---|---|---|---|---|
| c | 4-methylpyridin-3-yl | N/R | | | |
| d | pyridin-4-yl | 18.4 | 535 | 425 | 6.9 |
| e | phenyl | 22% | 542 | | very slow |

TABLE 2

| entry | R | isolated yield | δ_max | ε(M⁻¹cm⁻¹) |
|---|---|---|---|---|
| f | benzyl | 2.4% | 540 | 767 |
| g | naphthalen-2-ylmethyl | 48% | 537 | |
| h | 3,5-bis(trifluoromethyl)phenyl | 5.9% | 534 | 417 |
| i | 4'-(pentyloxy)-[1,1'-biphenyl]-4-yl | 0.5% | | |

Assymetric Tetrazines

| entry | R¹ | R² | isolated yield | δ_max | ε(M⁻¹cm⁻¹) (MeCN) | k₂(M⁻¹s⁻¹) |
|---|---|---|---|---|---|---|
| j | 3,5-bis(trifluoromethyl)phenyl | 4'-(pentyloxy)-[1,1'-biphenyl]-4-yl | 0.8% | 547 | | |

Other tetrazines include bptz and tz-2:

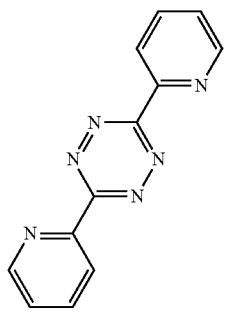
bptz

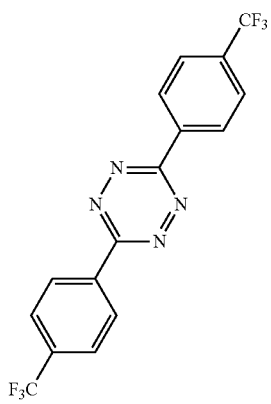
Tz-2

Additional dienes capable of Diels Alder reactions for sensing of alkenes can include structures that are highly electron deficient with electron accepting properties including the following structures. These materials additionally have extended aromatic structures that can promote favorable interactions with the conducting material that they are in contact with. After reaction with alkenes these materials can be less electron poor and the change in their electronic properties can serve to change the resistivity of the conducting materials. The conducting materials can be based on conducting polymers, carbon nanotubes, graphene, graphite, metal nanowires, metal oxides, or inorganic semiconductors.

As a result of their electron poor nature these molecules can be most effective in Diels-Alder reactions with alkenes that are substituted with electron neutral or donating groups. These alkene substituents can be other alkenes, alkyl groups, phenyl groups, or alkoxy groups. These molecules can react with cyclic alkenes including highly strained systems including 1-methyl cycloproprene.

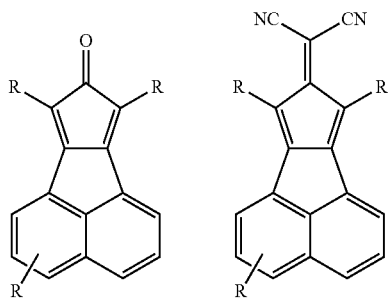

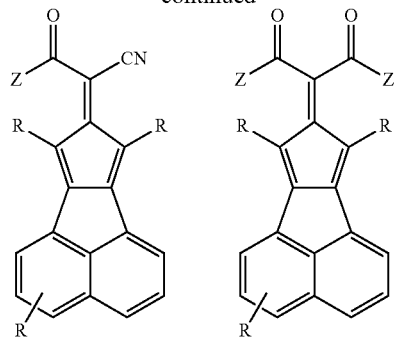

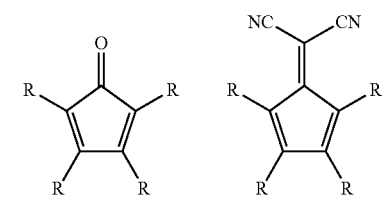

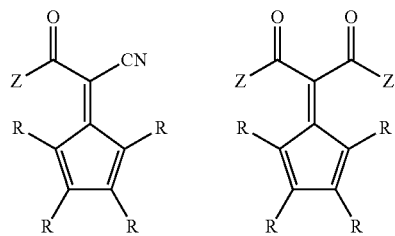

R=Aromatic, alkyl, fluoroalkyl, nitrile, ester, ketone, or halogen.

Z=Aromatic, alkyl, fluoroalkyl, $NR_2$, or OR.

Multiple R groups can be added to the aromatic rings and the different R or Z groups can be present in the same molecule. The aromatic can be a C6-C14 aryl, for example, phenyl or naphthyl. The alkyl can be a C1-C16 alkyl, for example, methyl, ethyl, propyl, butyl, pentyl or hexyl. The fluoroalkyl can be a fluorianted C1-C16 alkyl, for example, methyl, ethyl, propyl, butyl, pentyl or hexyl including 1, 2, 3, 4 or 5 fluoro groups.

A complement to the electron-poor molecules shown are electron-rich Diels-Alder dienes that are shown below. These molecules are not expected to undergo Diels-Alder reactions with ethylene and other electron rich alkenes. They are likely to be reactive with strained alkenes or electron deficient alkenes. Of particular interest are alkenes of the formula $CH_2CH(EWG)$, wherein EWG stands for an electron withdrawing group such as a ester, ketone, nitrile, or carboxylic acid. Electron deficient alkenes such as acrylates and acrylonitrile are toxic chemicals that can be used in the polymer and finishes industries. These dienes can have high reactivity with these analytes. Upon reaction, the electron donating properties of the diene can change and effect changes in the resisitivity of a conducting materials in which that are in contact. The conducting materials can be based on conducting polymers, carbon nanotubes, graphene, graphite, metal nanowires, metal oxides, or inorganic semiconductors.

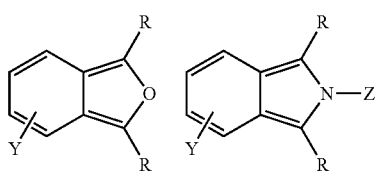

Y = Alkyl, Aryl, halogen, O-Alkyl, O-Aryl
R = Aromatic, alkyl
Z = CF$_2$, SO$_2$R

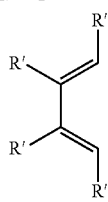

R' = Alkyl, O-Alkyl, O-Aryl, Amine

In both of the last sets or Diels-Alder dienes the reaction can cause a large change in the electronic structure of the diene. This change can cause a change in the optical properties of the molecules and can cause a change in the visible color of the compounds or changes in their fluorescence intensity. These changes can be used to detect the presence of an alkene analyte of interest.

It can be important to differentiate between electron poor DA dienes, often referred to as inverse demand DA dienes, and electron rich dienes. The inverse demand systems can be better with electron neutral or donating alkenes, whereas the electron rich systems can be better with electron poor alkenes which can be toxic.

Importance of Alkene and Ethylene Detection

Alkenes are an important feedstock, product, by-product, or transient species of many biological, laboratory scale, consumer, and industrial processes such as, but not limited to: biochemical pathways, internal combustion engine exhaust, industrial manufacturing processes including petrochemical refining, oil & gas discovery, extraction, polymer manufacture, etc. The ability to selectively detect and quantify their presence is of interest in enabling a wide variety of applications, for example, fruit ripeness determination, fruit & flower expiration date prediction, breath analysis, oil & gas well characterization, industrial safety, consumer safety at gas stations, exhaust characterization, and so on.

The detection and monitoring of ethylene is of great interest and importance in the food and agricultural industries. Ethylene as one of the smallest plant hormones is responsible for the ripening of fruit and plays an important role in many more developmental plant processes such as seed germination, fruit ripening, senescence and abscission. Measurement of the rate of ethylene evolution can be used as an indicator of fruit age. As fruits and vegetables start ripening, ethylene is produced and emitted, and the internal ethylene concentration in some fruits is used as a maturity index to determine the time of harvest. As ripening begins, the production of ethylene can increase dramatically. In some fruits and vegetables, such as bananas, the ripening process is continued after harvesting by exposure to ethylene gas, and the monitoring of ethylene gas in storage rooms is important to avoid deterioration of ethylene-sensitive produce.

Methods of Alkene and Ethylene Detection

Current methods for alkene differentiation and quantitation exist but are either prohibitively expensive for many applications of interest (GC-FID-MS), prohibitively complex and/or unsafe for on-site use (titration with oxidizing agents such as KMnO$_4$, Br$_2$), or not selective enough for sophisticated applications beyond determining whether an alkene is present (disposable alkene indicator tubes (Drager tubes), KMnO$_4$, Br$_2$).

Ethylene can be detected by different methods. A sensory system of ethylene can use fluorescent conjugated polymers. Esser, Birgit, and Timothy M Swager. "Detection of Ethylene Gas by Fluorescence Turn-On of a Conjugated Polymer." Angewandte Chemie International Edition 49.47 (2010): 8872-8875, which is incorporated by reference its entirety. The fluorescence of the conjugated polymer is partly quenched by the presence of copper (I) moieties that can coordinate to the polymer. Upon exposure to ethylene gas, the copper complexes bind to the ethylene molecules and no longer quench the polymer fluorescence. It requires a specific binding event to the copper to create a new signal whereas a fluorescence quench can take place. A chemoresistive sensor able to detect ethylene can be based on carbon nanotubes. Esser, Birgit, Jan M Schnorr, and Timothy M Swager. "Selective Detection of Ethylene Gas Using Carbon Nanotube-based Devices: Utility in Determination of Fruit Ripeness." Angewandte Chemie International Edition 51.23 (2012): 5752-5756, which is incorporated by reference in its entirety. The ethylene sensitive material is a mixture of SWNTs with a copper(I) complex 1 based upon a fluorinated tris(pyrazolyl) borate ligand, which is able to interact with the surface of carbon nanotubes, thereby influencing their conductivity. Upon exposure to ethylene, complex 1 binds to ethylene and forms complex 2, which has a decreased interaction with the SWNT surface.

Methods of ethylene detection include Gas chromatography, High-performance liquid chromatography, nuclear magnetic resonance, drager tubes, combustion analysis and titration methods. But these methods are either expensive, or provide low-quality information.

Another method of detecting an analyte in a sample include a carbon-carbon multiple bond moiety comprising exposing a detection region of a detector including a heteroaromatic compound having an extrudable group and capable of undergoing Diels-Alder reaction with the analyte including a carbon-carbon multiple bond moiety to the sample, and detecting color change of a reaction mixture comprising the heteroaromatic compound based on the presence of the analyte in the sample. This method provides alkene and alkyne detection, differentiation, and quantitation that addresses the growing need of transducing relevant information (only previously attainable from sophisticated methods such as GC-analysis) with the favorable low-cost and ease-of-use attributes ascribed to more basic technologies. Using this method, a device can indicate the presence of specific classes of alkenes or alkynes in the gas phase, and can determine the total exposure of the device to said alkenes or alkynes, based on a colorimetric readout. Because this device is selective for certain classes of alkenes and alkynes, it allows for differentiation of compounds of interest that contain certain alkene or alkyne functionality. This method can make use of the color change that accompanies the transformation of an s-tetrazine moiety to a pyrimidine moiety upon reaction with unsaturated carbon-carbon bonds.

This approach to alkene detection has a number of useful characteristics that make it desirable as a method of alkene quantitation and differentiation. Some of these advantages include, but are not limited to determining total exposure of an object to an alkene that may influence it's properties, health, or former, current, or future state of being and determining the presence of different classes of alkenes with easy to understand, inexpensive technology. In addition, when the extrudable group of the heteroaromatic compound is di-nitrogen, the by-product of the reaction with alkyne or alkene, such as ethylene, is $N_2$, which is food safe.

Property Change after Diels-Alder Reaction

The properties of a detection region can change after the Diels-Alder reaction takes place. The property change can be a color change, fluorescence change, conductivity change or a combination thereof.

The extent of property change before and after Diels-Alder reactions can vary with different additives. Different colors can be obtained by adding a copper salt, a nickel salt, a silver salt, a zinc salt, an aluminum salt, or a gold salt to the reaction mixture. Examples of the additive include silver triflate (AgOTf), silver trifluoroacetate ($AgOCOCF_3$), silver perchlorate ($AgClO_4$), silver hexafluorophosphate ($AgPF_6$), silver sulfate ($Ag_2SO_4$), Nickel(II) triflate ($Ni(OTf)_2$), copper(II) triflate ($Cu(OTf)_2$), zinc triflate ($Zn(OTf)_2$), or aluminum ethoxide ($Al(OEt)_3$). Conductivity changes can be monitored by including a conductive material, such as a carbon nanotube, graphite, graphene, semiconductor nanowire, metal nanowire, or conducting polymer. Fluorescence changes can be monitored by including a luminescent material, such as a conjugated molecule, a conjugated polymer, or an inorganic phosphor. The region is then monitored for color, absorbance, fluorescence, conductivity, or a combination thereof.

Methods of Quantifying the Amount of an Analyte

The amount of an analyte, such as ethylene, can be quantified based on the color change. Alkenes of interest can be differentiated by correlating alkene reactivity with initial and final properties of the reaction (herein described as "reaction property profile"). The composition of matter that is responsible for these reaction property profiles. This disclosure describes the manner in which devices may exploit these reaction property profiles such that a readout can be used to detect alkenes selectively and determine cumulative device exposure to alkenes. The detection can be colorimetric, fluorescence, or conductivity.

Colorimetric systems can have certain advantages. Using standard image processing software, the photographs can be used to determine the RGB values of the reaction mixtures. The RGB color space value can be used as one variable to differentiate alkene and/or alkyne classes.

Euclidean distance is one variable that can be used to differentiate alkene and/or alkyne classes. In addition, Euclidean distance is one variable that can be used to determine extent of reaction and therefore cumulative ethylene exposure to the device to quantify ethylene, preferably if starting quantities of alkene detecting material are known.

Absorption-based concentration measurement can also be used to quantify an analyte, such as ethylene. The absorbance of a material varies linearly with both the cell path length and the analyte concentration. These two relationships can be combined to yield a general equation of Beer's Law.

$$A = \varepsilon l c$$

A is the absorbance of the solution and is measured by a spectrometer. The quantity $\varepsilon$ is the molar absorptivity or the extinction coefficient; l is the length of solution light passes through (cm); c is concentration of the solution. As the reaction proceeds, the concentration of the solution changes, which can be detected through spectroscopic measurement.

UV-VIS spectroscopic measurements of a solution can be used to determine the observed rate constant, $k_{obs}$, which can then be used in subsequent calculations to determine the second-order rate constant, $k_2$. Each combination of compound and/or complex X and alkene and/or alkyne Y has a unique $k_2$. Thus, $k_2$ can be one variable on which to differentiate alkene and/or alkyne classes.

A Detector for Detecting an Analyte

A detector for detecting an analyte can include a housing including a detection region comprising a compound having an extrudable group and capable of undergoing Diels-Alder reaction with the analyte including a carbon-carbon multiple bond moiety. The housing can be a tube, solid, formulation, solid support, or solid substrates. The device can be incorporated into solid formulations or solid supports or substrates, such as paper, plastic, rubber, virtually any kind of polymer not containing sufficiently reactive alkenes and/or alkynes, as well as liquids such as inks.

FIG. 1 is a block diagram showing one example of a detecting device. In FIG. 1, 10 is a housing, which can be a tube, solid, formulation, solid support, or solid substrates, as well as liquids such as inks, and 20 is a detection region where a compound having an extrudable group can undergo a Diels-Alder reaction with the analyte including a carbon-carbon multiple bond moiety.

EXAMPLES

Selective Reaction and Detection of an Analyte

Figure 2:
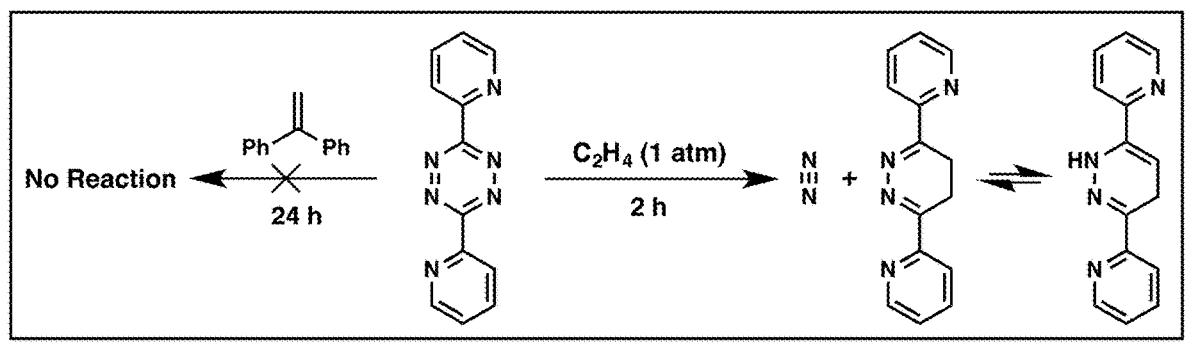
FIG. 2 is a demonstration of selective alkene detection.

FIG. 2 is a demonstration of selective alkene detection. To Bptz dissolved in solvent was added alkene (molar excess). Experiments were conducted under ambient atmosphere and temperature, except in the case of $C_2H_4$, which was sparged through solution for 30 s at 50 SCFH and left under 1 atm of ethylene. Results were observed and recorded after 6.5 hours of reaction. A sterically unencumbered alkene ($C_2H_4$) readily reacts with Bptz. A sterically congested alkene (1,1'-diphenylethylene) does not.

Color Change after Diels-Alder Reaction

Figure 3:
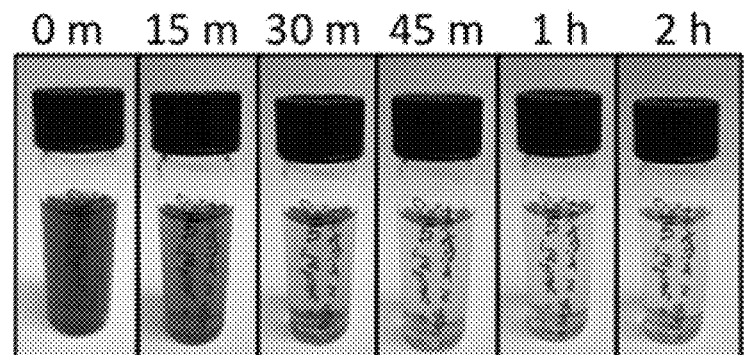
FIG. 3(a) shows time based color change when the solution contains silver triflate and bptz.
FIG. 3(b) shows one reaction example.
Figure 3:
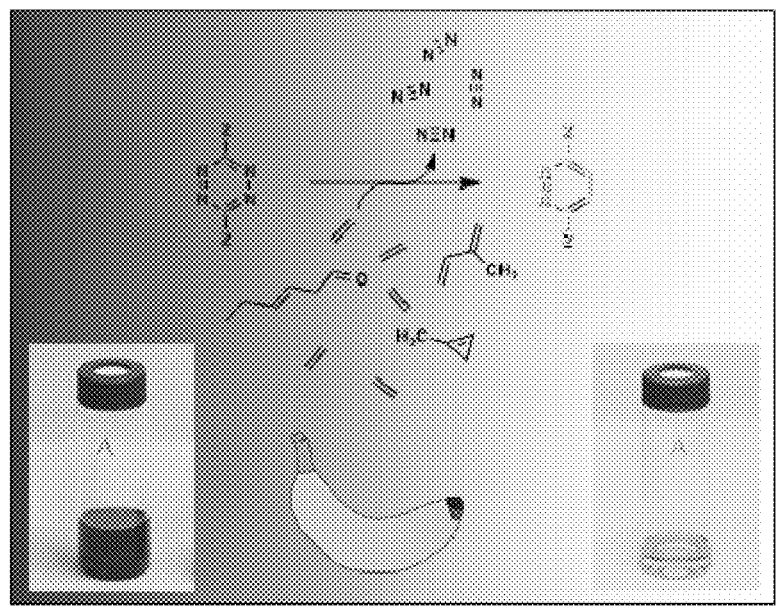
Figure 4:
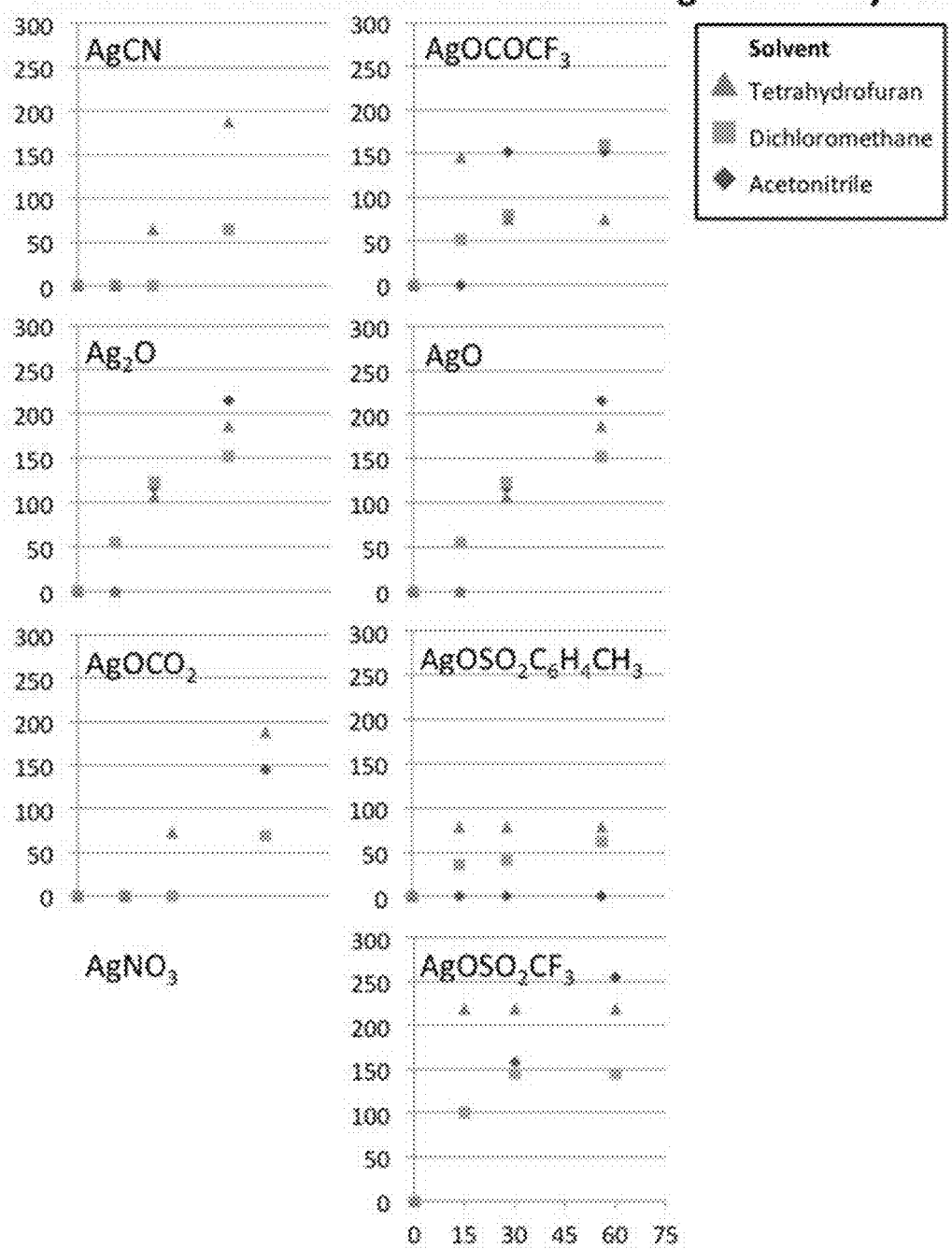
FIG. 4 shows the extent of color change post-ethylene addition when the solution contains different kinds of silver salt.

FIG. 3(a) shows time based color change when the solution contains silver triflate and bptz. FIG. 3(b) shows one reaction example. FIG. 4 shows the extent of color change post-ethylene addition when the solution contains different kinds of silver salt.

Quantify the Amount of an Analyte

Figure 5:
FIG. 5 shows photographs of vials containing bis-2-pyridyl-1,2,4,5-tetrazine (bptz) and additive in dichloromethane, before exposure to ethylene and after 1.5 h of exposure to a headspace of $C_2H_4$ (1 atm) at room temperature.
Figure 6:
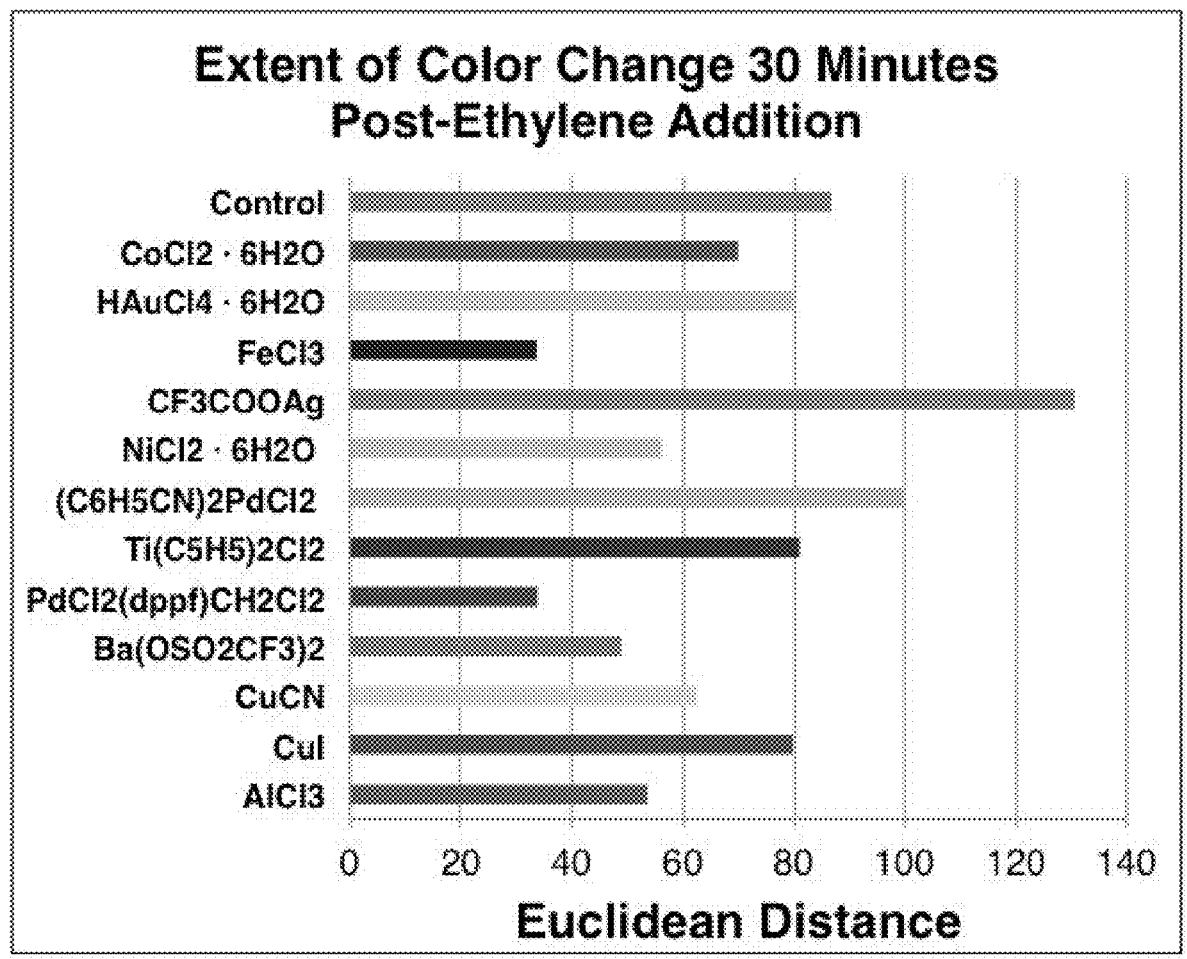
FIG. 6 shows euclidean distance as a quantitative representation of reaction color profile.

FIG. 5 shows photographs of vials containing bis-2-pyridyl-1,2,4,5-tetrazine and additive in dichloromethane, before exposure to ethylene and after 1.5 h of exposure to a headspace of $C_2H_4$ (1 atm) at room temperature. Using standard image processing software, the photographs can be used to determine the RGB values of the reaction mixtures. The RGB color space value can be used as one variable to differentiate alkene and/or alkyne classes. FIG. 6 shows euclidean distance as a quantitative representation of "reaction color profile."

In FIG. 5 and FIG. 6, to an oven dried Teflon stir bar equipped, Teflon septum equipped scintillation vial that was evacuated and backfilled with argon (×1) was added metal salt (M). Each metal salt was weighed out in duplicate (one for vial containing M+Bptz and one for control containing solely M). Separately, a 250-mL round bottom flask (RBF) was equipped with a Teflon-coated stir bar and rubber septum, evacuated and backfilled with argon, and flame dried under vacuum. To it was added Bptz (178.1 mg) and dry dichloromethane (DCM) (150.0 mL) via cannula, to furnish a 0.05 M stock solution of Bptz (bright pink homogenous solution). To each vial containing M was added 0.05

M Bptz solution (10 mL) and each was stirred vigorously for 10 minutes, resulting in a range of colors (see FIG. 5, t=0 h). Each solution was then sparged with $C_2H_4$ for 30 s at a flow rate of 50 SCFH. The solutions were then photographed once per minute for 2 hours.

From the photographs, the solution colors were quantified in Adobe Photoshop using the color picker function to generate RGB color space values. The average of three picked values was used for each reported value. The total Euclidean distance (d) traveled over the course of the reaction (net reaction color profile) was determined by equation 1:

$$d(C_f C_i) = \text{square root}[(r_f-r_i)^2+(g_f-g_i)^2+(b_f-b_i)^2] \quad (1)$$

Where C stands for color; r, g, b, stand for red, green, and blue, respectively; and the subscripts $_f$ and $_i$ denote final and initial.

Figure 7:
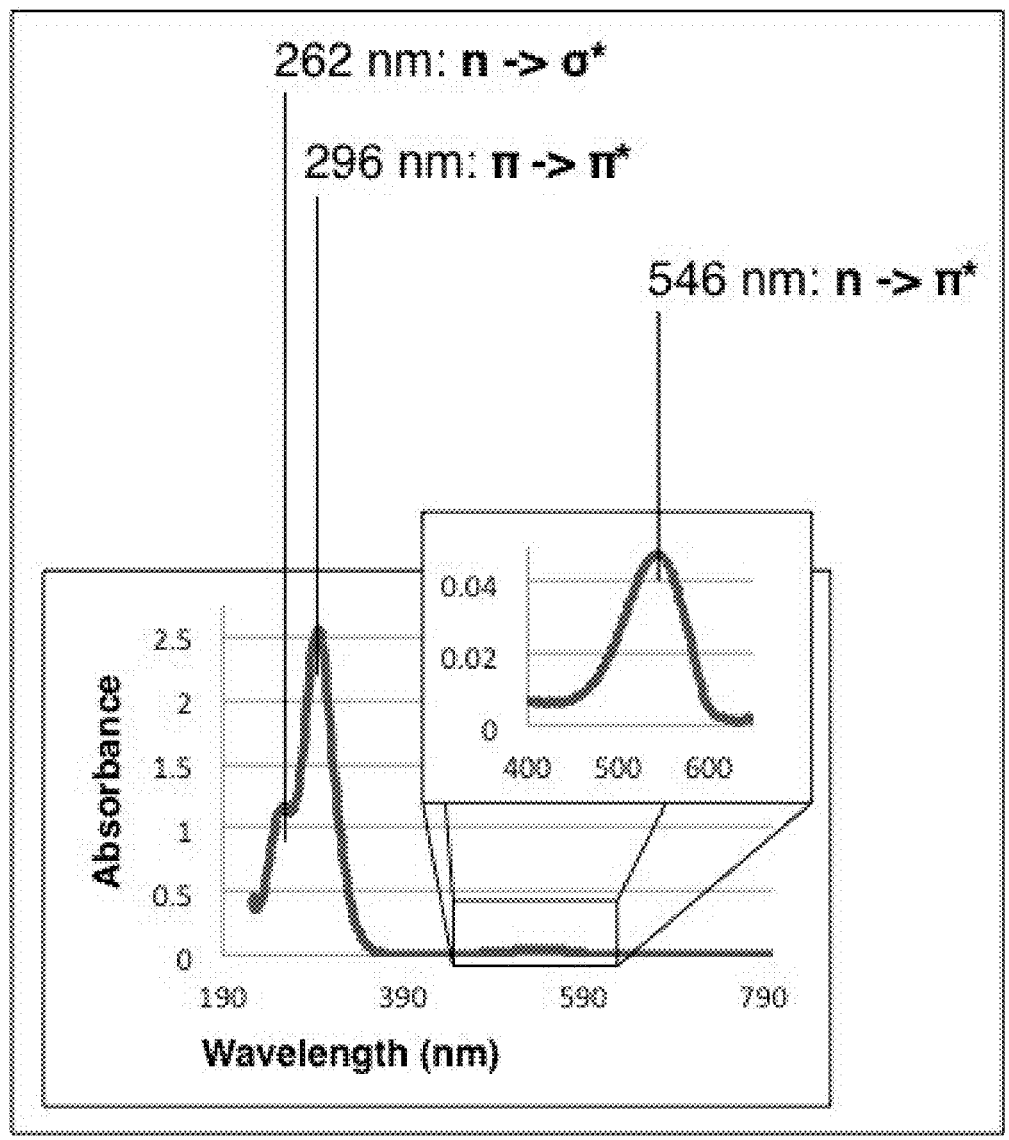
FIG. 7 shows a representative example of a UV-VIS spectrum of Bptz in organic solvent.

FIG. 7 shows representative example of a UV-VIS spectrum of Bptz in organic solvent. Depicted are the three primary absorption bands that can be used to monitor the course of the reaction. The color perceived by the human eye is due to the absorption band which has a $\lambda_{max}$ at ~546 nm.

Figure 8:
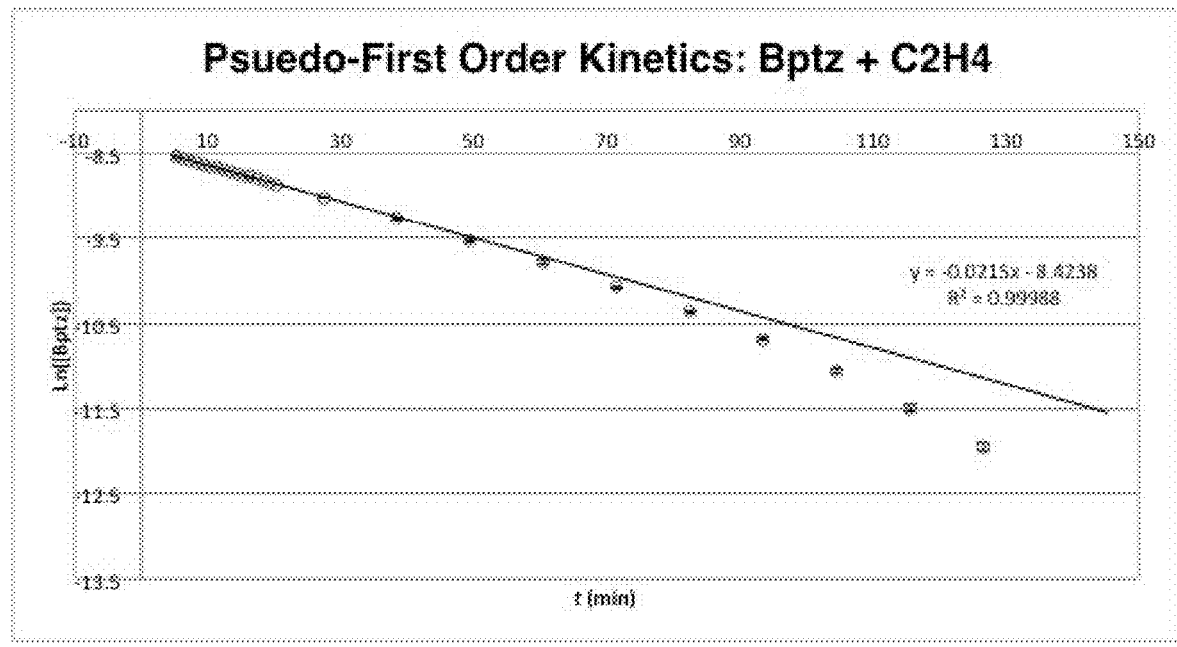
FIG. 8 shows graphical representation of UV-VIS spectroscopic measurements of $\lambda_{max}$ ($\lambda_{max}$=545 nm) of a solution of Bptz in acetonitrile (MeCN) when exposed to a gross molar excess of $C_2H_4$ (1 atm) over time.

FIG. 8 shows graphical representation of UV-VIS spectroscopic measurements of $\lambda_{max}$ ($\lambda_{max}$=545 nm) of a solution of Bptz in acetonitrile (MeCN) when exposed to a gross molar excess of $C_2H_4$ (1 atm) over time. To an ethylene purged, quartz cuvette (4 mL) equipped with silicone septum was added Bptz in acetonitrile (MeCN) (200 uM) (2 mL). The vial was shaken rapidly, and the absorbance at 538 nm was observed at time intervals (1 s) for 130 m. Using the molar absorptivity, the absorbance values were then converted to concentration of Bptz, [Bptz], and the plot of Ln([Bptz]) vs. t depicted was generated. Performing a linear regression on data points from t=0 to t=15 m yielded a line with a slope that is $k_{obs}$. $k_{obs}$ can then be used in subsequent calculations to determine the second-order rate constant, $k_2$. Each combination of compound and/or complex X and alkene and/or alkyne Y has a unique $k_2$. Thus, $k_2$ can be one variable on which to differentiate alkene and/or alkyne classes.

Figure 9:
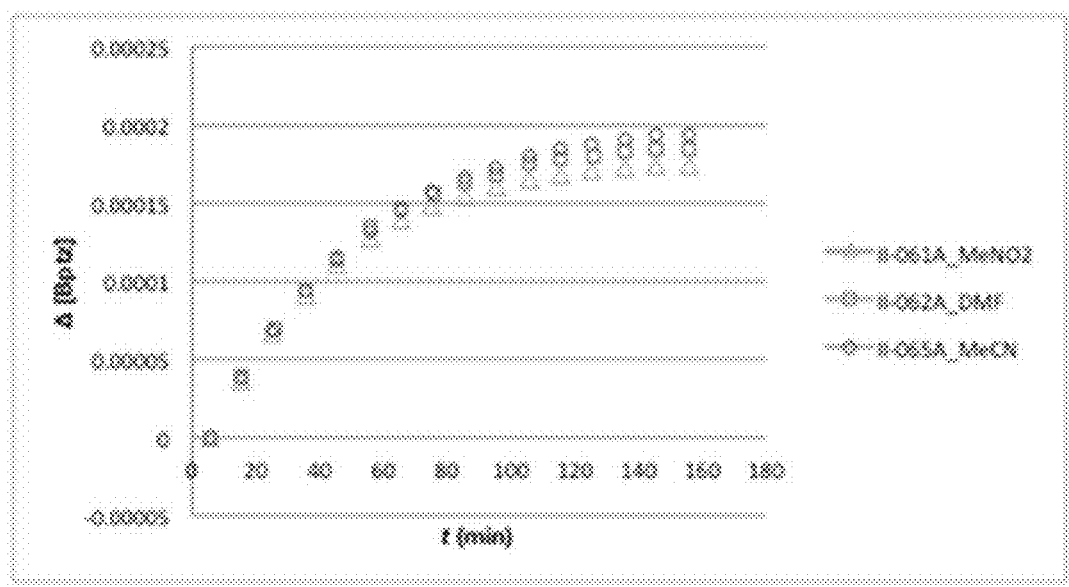
FIG. 9 shows kinetics experiment results in nitromethane ($MeNO_2$), dimethylformamide (DMF), and acetonitrile (MeCN).

FIG. 9 shows kinetics experiment results in Nitromethane ($MeNO_2$), Dimethylformamide (DMF), and MeCN. Cuvette (4 mL) equipped with silicone septum was purged with $C_2H_4$; bptz in solvent (2 mL; 200 uM) was injected into cuvette equipped with bubbler; cuvette was shaken up and down rapidly; measurement then began immediately at $\lambda_{max}$ (nm).

Color Based Detectors for Detecting an Analyte

Figure 10:
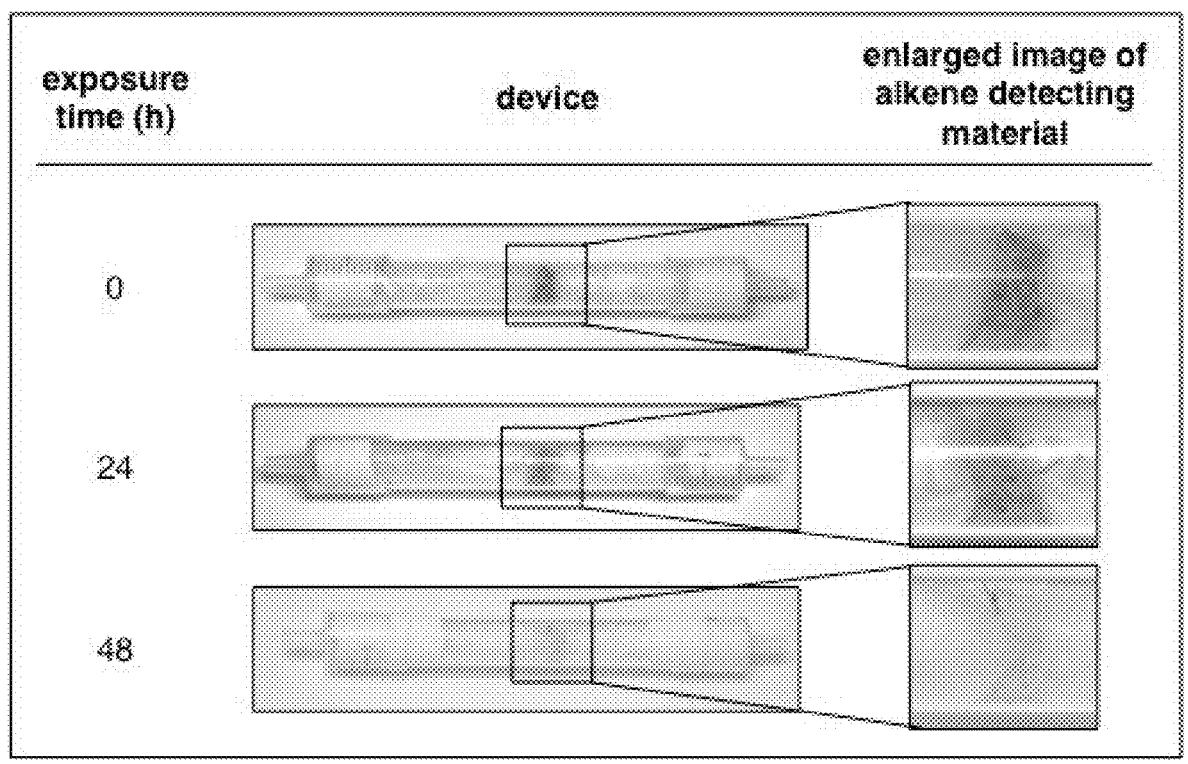
FIG. 10 shows photographs of alkene sensing material incorporated into a glass tube containing glass wool.

FIG. 10 shows photographs of alkene sensing material incorporated into a glass tube containing glass wool (glass wool surrounding the pink-colored alkene sensing material). The depicted glass tube (device) is equipped with Leur-type syringe tips, enabling connection to gas-stream inlet and outlet tubing. The device was exposed to a continuous stream of 1,000 ppm $C_2H_4$ in $N_2$ carrier gas at a flow rate of 0.5 L/min. An indicating amount of Bptz impregnated polystyrene fibers was added to the glass tube containing glass wool. These fibers were the by-product of the fabrication process described in the experimental pertaining to FIG. 11. The tube was capped with modified plastic syringe tips, and was equipped to a KinTech gas mixer. The tube was then subjected to 1,000 ppm $C_2H_4$ in $N_2$ at a flow rate of 0.5 L/min. Photographs were taken at t=0 h, 24 h, and 48 h to monitor the decolorization process.

Figure 11:
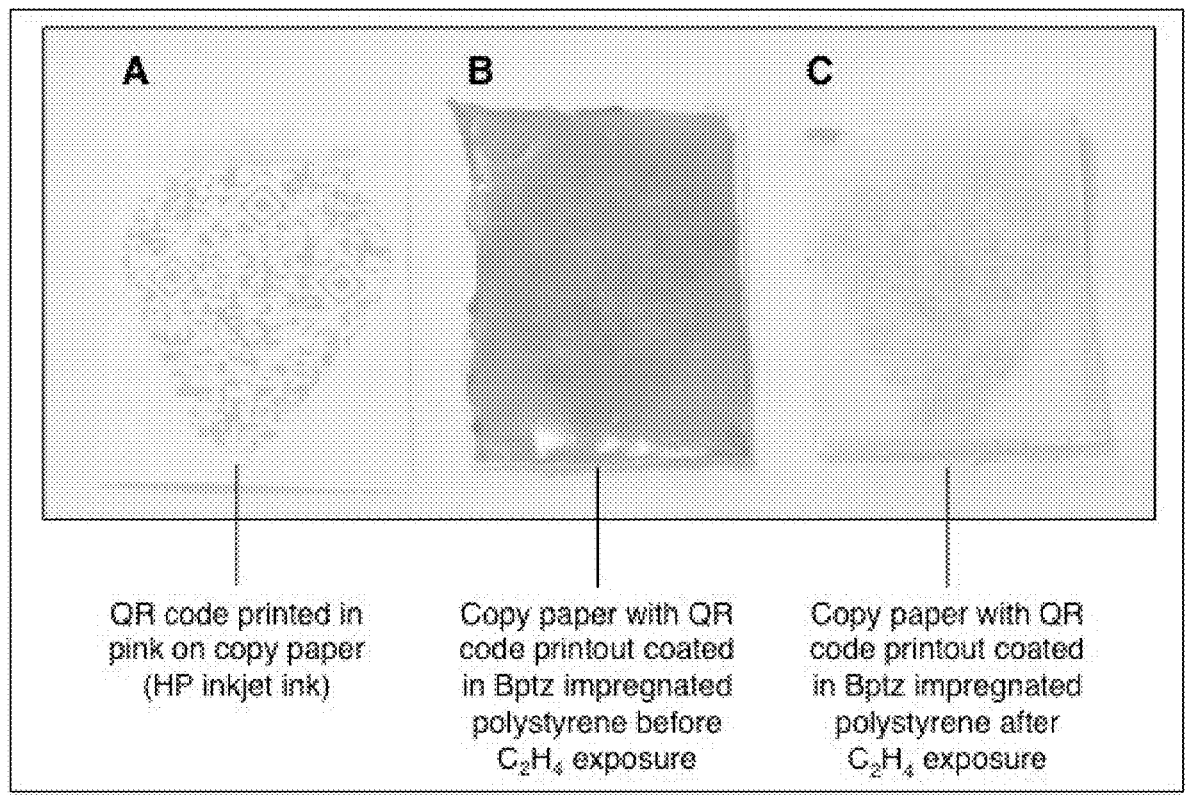
FIG. 11(A) shows a photograph of QR code printed in pink on copy paper.
FIG. 11(B) shows a photograph of Bptz impregnated polystyrene coating covering a printed Quick Read (QR) code on copy paper before exposure to $C_2H_4$.
FIG. 11(C) shows a photograph of Bptz impregnated polystyrene coating covering a printed QR code on copy paper after exposure to $C_2H_4$ (1 atm) for 1 h.

FIG. 11 shows photographs of Bptz impregnated polystyrene coating covering a printed QR code on copy paper. FIG. 11(A) shows a photograph of QR code printed in pink on copy paper. Before exposure to $C_2H_4$, the coating is pink and the QR code is unreadable, as shown in FIG. 11(B). After exposure to $C_2H_4$ (1 atm) for 1 h, the polystyrene coating has decolorized, rendering the QR code readable by machines (e.g. personal hand-held devices such as camera phones), as shown in FIG. 11(C). To a solution of Bptz in DCM (0.01 M) was added polystyrene such that the final volume ratio was 4:1 solution:polystyrene (v/v), resulting in a pink, viscous, homogenous solution. Separately, a piece of copy paper with printed QR code had been affixed with double sided tape to a glass cover slide and fitted to a spin-coater. The copy paper sample was spun at 2,000 rpm and the stock solution described above was expelled from a syringe directly onto it from above, at a rate of ~1 mL/min. After removing any remaining DCM under vacuum, the resulting plastic coated QR code was exposed to $C_2H_4$ (1 atm) in an air-tight glass container for 2 hours. Before and after photographs were taken to document the color change.

Figure 12:
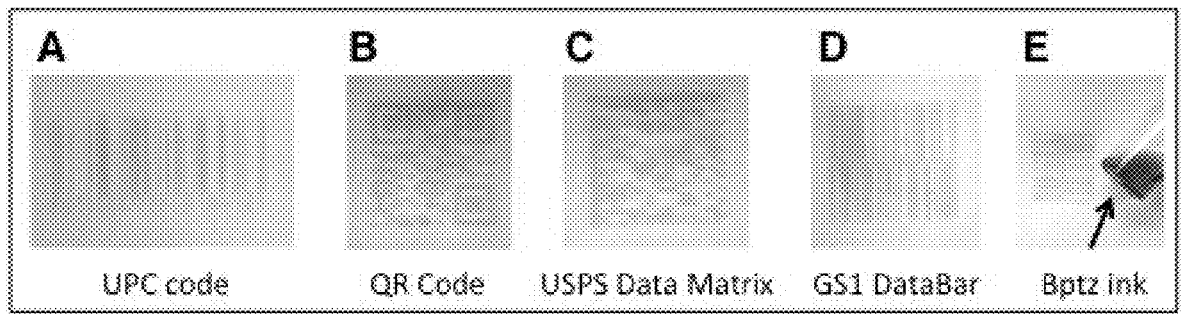
FIG. 12(A) shows a photograph of UPC code.
FIG. 12(B) shows a photograph of Quick Read (QR) code.
FIG. 12(C) shows a photograph of USPC data matrix.
FIG. 12(D) shows a photograph of GS1 DataBar.
FIG. 12(E) shows a photograph depicting Bptz ink (pink colored solution indicated by arrow) with an example of a GS1 DataBar that it was used to print on copy paper.

FIG. 12 shows photographs of various standardized, machine-readable representations of data printed using inks created with Bptz as pigment: UPC code in FIG. 12(A), Quick Read (QR) code in FIG. 12(B), USPS data matrix in FIG. 12(C), and GS1 DataBar in FIG. 12(D). FIG. 12(E) shows a photograph depicting Bptz ink (pink colored solution indicated by arrow) with an example of a GS1 DataBar that it was used to print on copy paper.

Figure 13:
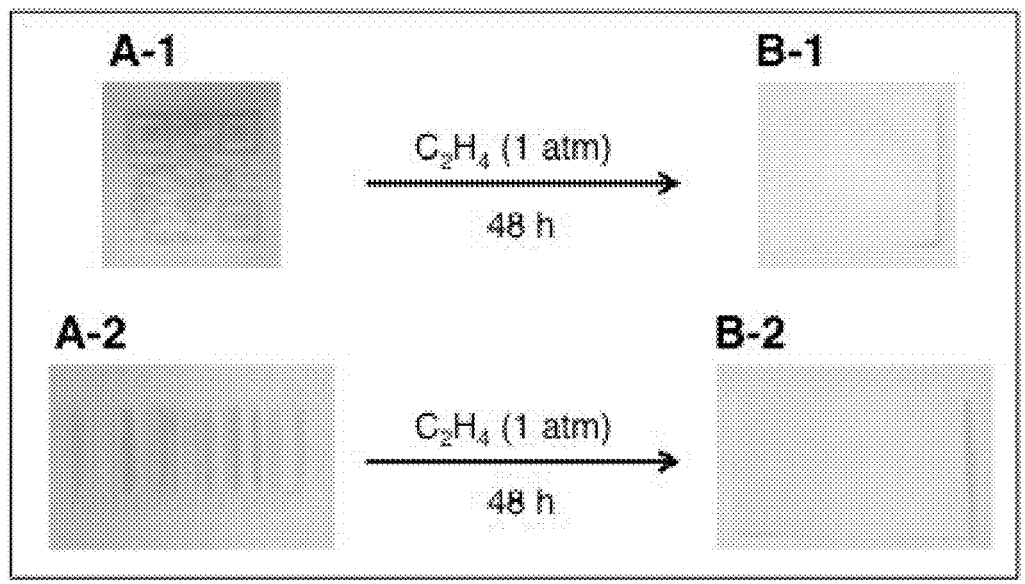
FIG. 13(A-1) and FIG. 13(A-2) shows photographs of standardized, machine-readable representations of data printed using inks created with Bptz as pigment before exposure to $C_2H_4$.

FIG. 13(A-1) and FIG. 13(A-2) shows photographs of standardized, machine-readable representations of data printed using inks created with Bptz as pigment before exposure to $C_2H_4$; FIG. 13(B-1) and FIG. 13(B-2) shows photographs of the representations after exposure to $C_2H_4$ (1 atm) for 48 h.

Accompanying FIG. 12 and FIG. 13, an empty HP desktop inkjet printer cartridge was charged with a solution of Bptz in 2:1 (v/v) $H_2O$:Acetone (0.01 M). It was quickly loaded into an HP inkjet printer, and the depicted images were printed in greyscale from a .PDF file, resulting in light-pink images on copy paper. The images were made darker by printing the same image multiple times (5-10 passes). The tetrazine-printed images (i.e. codified information) were exposed to $C_2H_4$ (1 atm) in a sealed glass container for 2 d, resulting in a color change from pink to faint yellow.

Effect of Acids

Figure 14:
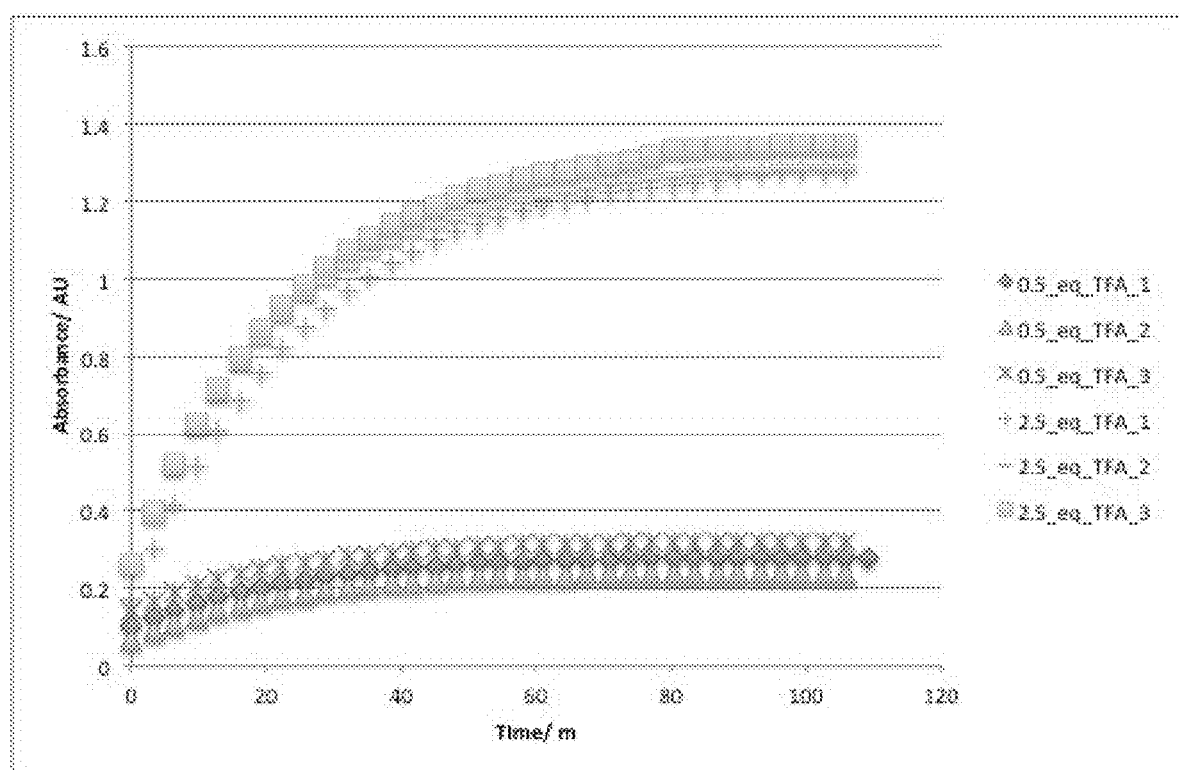
FIG. 14 is a UV-VIS kinetics plot showing change in absorbance over time after exposure of a solution of Bptz in the presence of two different molar equivalents of trifluoroacetic acid to ethylene gas, monitoring a single wavelength at 410 nm.

To an ethylene purged quartz cuvette equipped with silicone septum was added a solution of Bptz+trifluoroacetic acid (TFA) (200 uM in Bptz) in toluene (2 mL). Two and one-half molar equivalents of TFA were evaluated, and the growth of the UV-VIS absorption band at 410 nm was observed over time, to yield insight into the dependence of $k_{obs}$ on the presence of Bronsted acid. FIG. 14 is a graph showing a rate enhancement when Bptz is in the presence of Bronsted acid, in this case TFA. It shows that this rate enhancement is dependent on the molar equivalents of TFA present.

Figure 15:
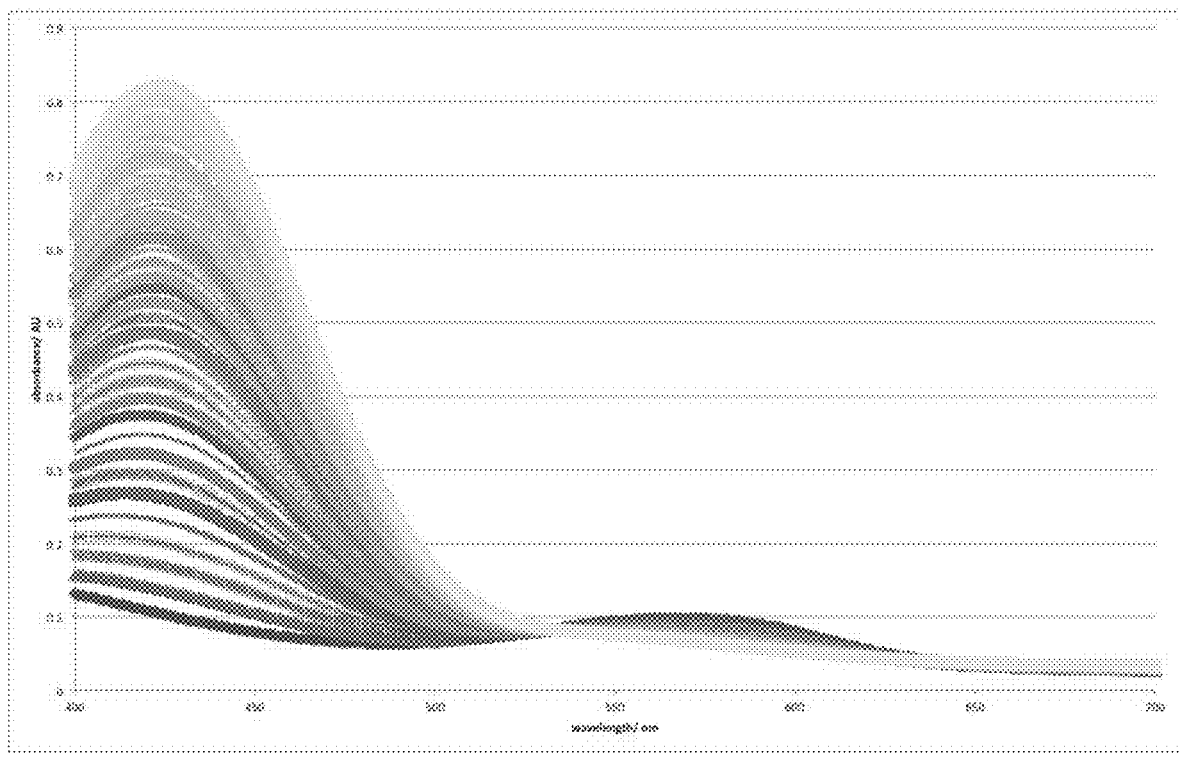
FIG. 15 is a graph depicting a time-course experiment showing the change in the UV-VIS spectra of a solution of 1:1 Bptz:$AgOCOCF_3$ in $MeNO_2$ after exposure to 1-hexene. 0.1 minute increments.

In another example, a quartz cuvette containing a solution of Bptz+$AgOCOCF_3$ (1:1; 0.5 mM in Bptz) was charged with 1-hexene. UV-VIS measurements were started immediately, and were recorded at 0.1 m intervals for 15 m. FIG. 15 shows the change in UV-VIS spectra of 1:1 bptz: $AgOCOCF_3$ over a 15 minute time course. It shows that a new, strong absorption band forms in the visible (~420 nm) which has a strong molar absorptivity. Thus, using silver salts allows us to monitor two variables simultaneously: disappearance of absorption band at 545 nm, and appearance of a new, stronger band at 420 nm. Note also that there is a rate enhancement associated with the silver salt, as this reaction was done in 15 minutes as opposed to the usual 1 h for naked Bptz. In general, Lewis acids can be rate-enhancing additives.

Fabrication of Selective Alkene Chemiresistors from Nanostructured Carbon and Alkene Selector Molecules Evaporation of Gold on Paper.

Gold (Au) electrodes were deposited on paper. See, for example, Mirica, K. A. et al., *Proc. Natl. Acad. Sci.* 2013, E3265-E3270, which is incorporated by reference in its entirety.

Stock Solution.

To a scintillation vial (20-mL) was added pristine single-walled carbon nanotubes (SWCNTs) (3.98 mg) and ortho-dichlorobenzene (o-DCB). The vial was capped with a plastic screw-cap, and sonicated in a water bath at room temperature for 10 minutes, resulting in a black heterogenous solution. To a separate scintillation vial (20-mL) was added alkene selector molecule (e.g. tetrazine) (S) (2.02 mg), o-DCB (1.5 mL) and chloroform ($CHCl_3$) (0.5 mL). The vial was capped with a plastic screw-cap and sonicated in a water bath at room temperature for 10 minutes, resulting in a colored homogenous solution (color dependent on S). The above solutions were combined by way of a plastic syringe or glass pipette and mixed thoroughly with a magnetic stir bar or by inverting (×10) to form a black heterogenous stock solution.

Fabrication of an Array of Sensors.

Sensors were fabricated by dropcasting the freshly made stock solution with a capillary tube (5 μL) in between gold electrodes on a substrate (weigh paper or glass). The solvent was removed by placing the electrodes into an evacuated chamber. After removal of the solvent, residual material was visibly adhered onto the surface of the substrate, bridging the gold electrodes. The resistance of the chemiresistor, R, was measured using a multimeter. The above process was repeated until 1.0 kΩ<R<20.0 kΩ for each sensor.

Sensing Measurements.

The array of sensors was mounted onto a glass slide (25 mm×75 mm×1 mm) with double-sided Scotch tape. The array was then inserted into a 2×30 pin edge connector, which made electrical contact with each of the gold electrodes within the array. The edge connector was then connected to the potentiostat via a breadboard (DigiKey). For sensing measurements, the devices were enclosed within a custom-made gas-tight Teflon chamber containing an inlet and outlet port for gas flow. The inlet port was connected to a gas delivery system, and the outlet port was connected to an exhaust vent. Measurements of conductance were performed under a constant applied voltage of 0.1 V using PalmSense EmStat-MUX equipped with a 16-channel multiplexer (Palm Instruments BV, The Netherlands). Data acquisition was done using PSTrace 2.4 software provided by Palm Instruments.

Delivery of Ethylene.

Delivery of controlled concentrations of ethylene to devices was carried out using Smart-Trak Series 100 gas mixing system at total flow rates between 2.0 mL/min and 1.0 L/min.

Figure 16:
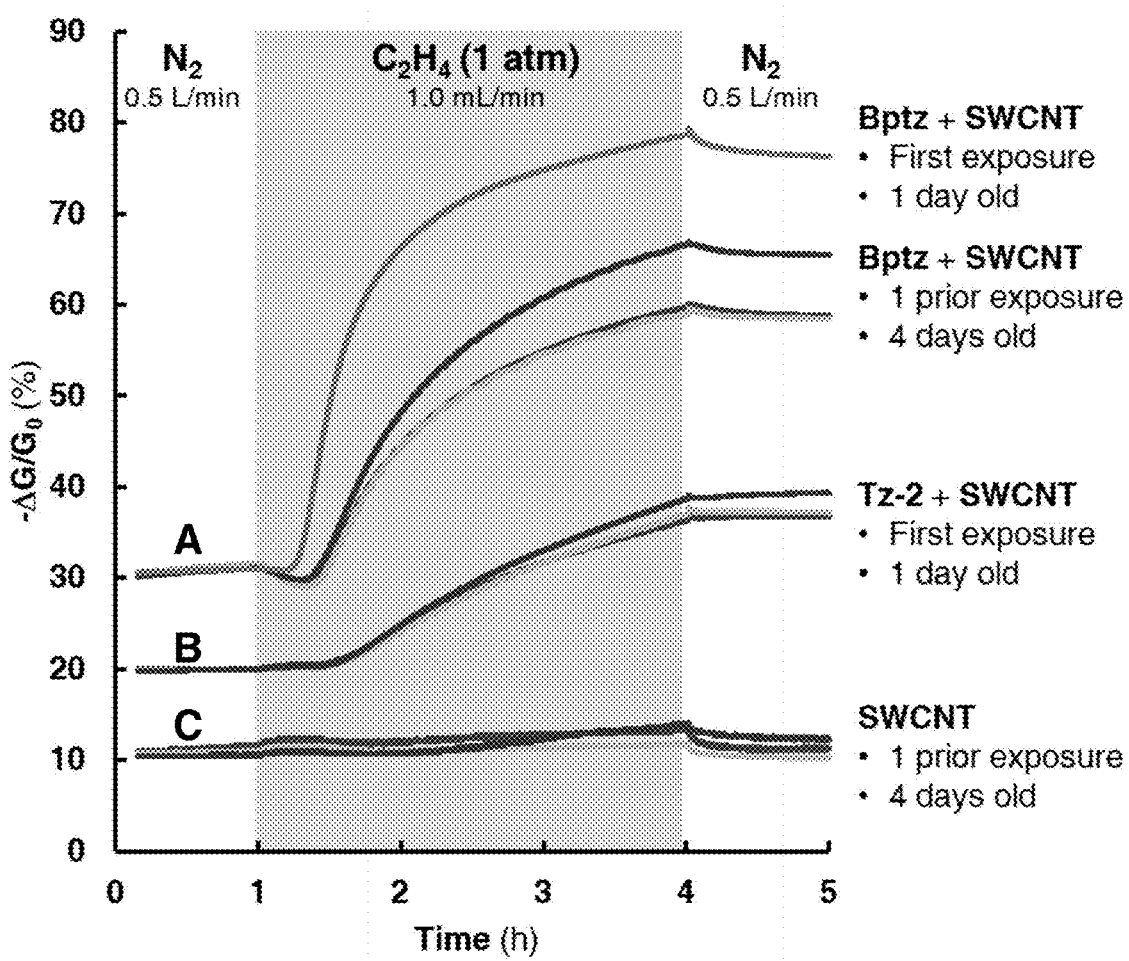
FIG. 16 shows photographs of a graph depicting test results of exemplary sensors.

FIG. 16 shows test results of sensors deposited using drop-cast (o-DCB/$CHCl_3$), with weigh paper as substrate, and Au (120 nm) as electrodes. SWCNT, ultrapure, was obtained from NanoC, and bptz, 96%, was obtained from Aldrich. Sensor composition 1:10 Tz/C (mol/mol) was used. Tz is generic for any tetrazine, such as Bptz or Tz-2. C is "moles of carbon atoms in SWCNTs" and is the generic case. FIG. 16 shows that SWCNT-bptz mixtures become less conductive in the presence of ethylene. In FIG. 16, a device fabricated one day prior to use (Group A, green trace) with a Bptz/SWCNT (2:1 Bptz/SWCNT (wt/wt)) chemiresistor displayed a dosimetric response toward pure ethylene (1 atm), with a 50% change in conductivity with respect to it's original state. Similarly, three devices fabricated four days prior to use with Bptz/SWCNT chemiresistors ((2:1 Bptz/SWCNT (wt/wt)) displayed dosimetric responses toward pure ethylene (1 atm), with a 35% change in conductivity with respect to it's original condition for one device (Group A; red trace), and a 30% change in conductivity with respect to their original conditions (Group A; yellow and blue traces) for the other two devices. Three devices fabricated one day prior to use with Tz-2/SWCNT chemiresistors (2:1 Tz-2/SWCNT (wt/wt)) displayed dosimetric responses toward pure ethylene (1 atm), with a 15% change in conductivity with respect to their original conditions (Group B; red, yellow, and blue traces). Three devices fabricated with pristine SWCNTs four days prior to use were employed as a negative control (Group C; red, yellow, and blue traces). They did not display a dosimetric response; rather, they displayed a reversible response that was less than 3% change in conductivity relative to their original conditions.

Figure 17:
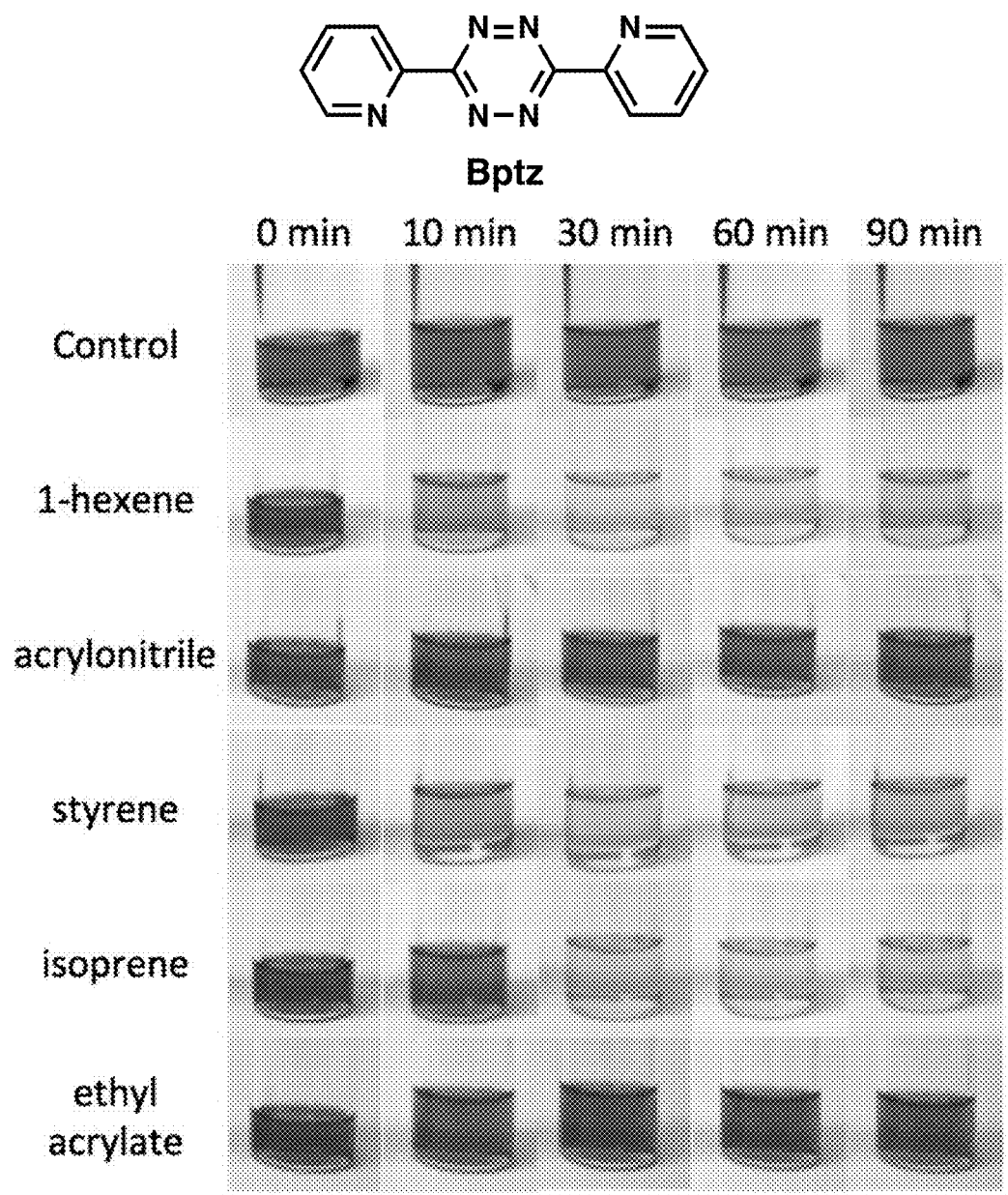
FIG. 17 shows photographs of a demonstration of selective electron-rich alkene detection.

FIG. 17 is a demonstration of selective electron-rich alkene detection. To Bptz dissolved in chloroform (5 mM) was added alkene (molar excess). Experiments were conducted under ambient atmosphere and temperature. Results were observed and recorded with a digital camera after 0, 10, 30, 60, and 90 minutes of reaction. Electron-rich alkenes (1-hexene, isoprene, styrene) reacted readily with Bptz. Electron-poor alkenes (acrylonitrile, ethyl acrylate) reacted slowly or not at all.

Figure 18:
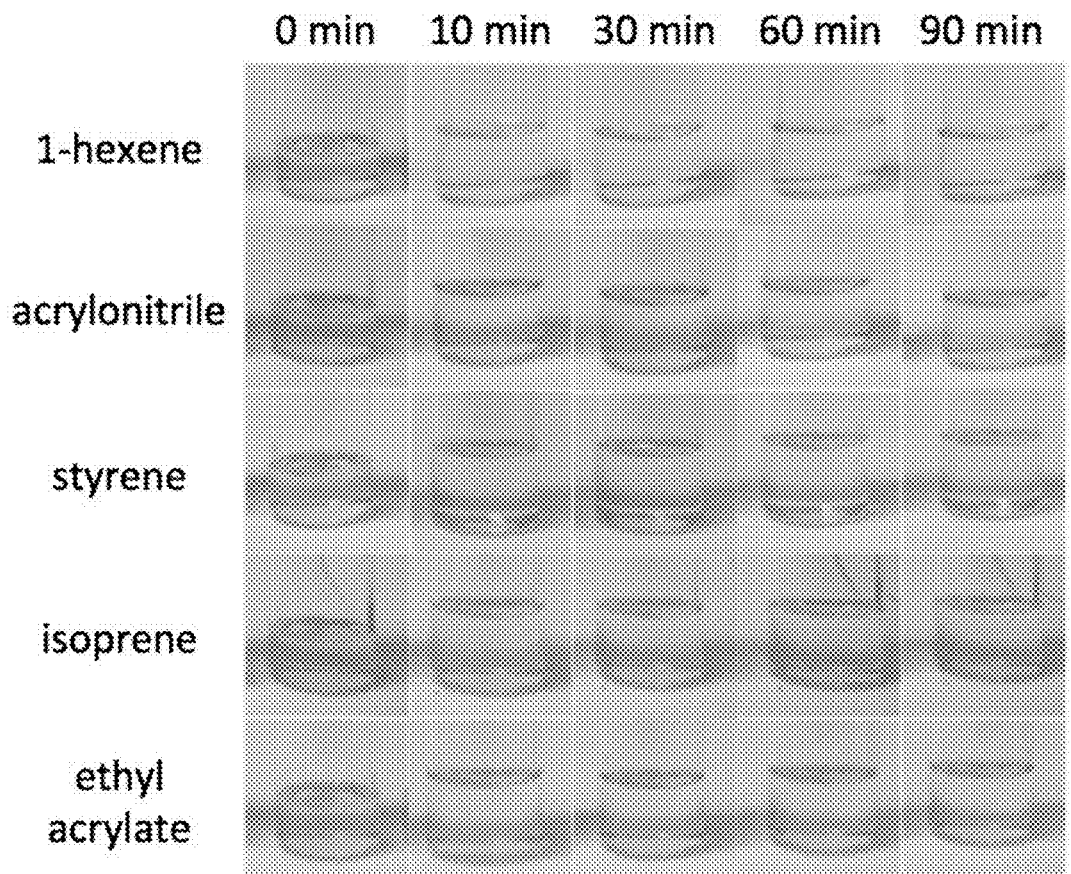
FIG. 18 shows photographs of a demonstration of selective electron-poor alkene detection.

FIG. 18 is a demonstration of selective electron-poor alkene detection. To 1,3-diphenylisobenzofuran (1 mM) dissolved in chloroform was added alkene (molar excess). Experiments were conducted under ambient atmosphere and temperature. Results were observed and recorded with a digital camera after 0, 10, 30, 60, and 90 minutes of reaction. Electron-poor alkenes (acrylonitrile, ethyl acrylate) reacted readily with 1,3-diphenylisobenzofuran. Electron-rich alkenes (1-hexene, isoprene, styrene) reacted slowly or not at all.

Figure 19:
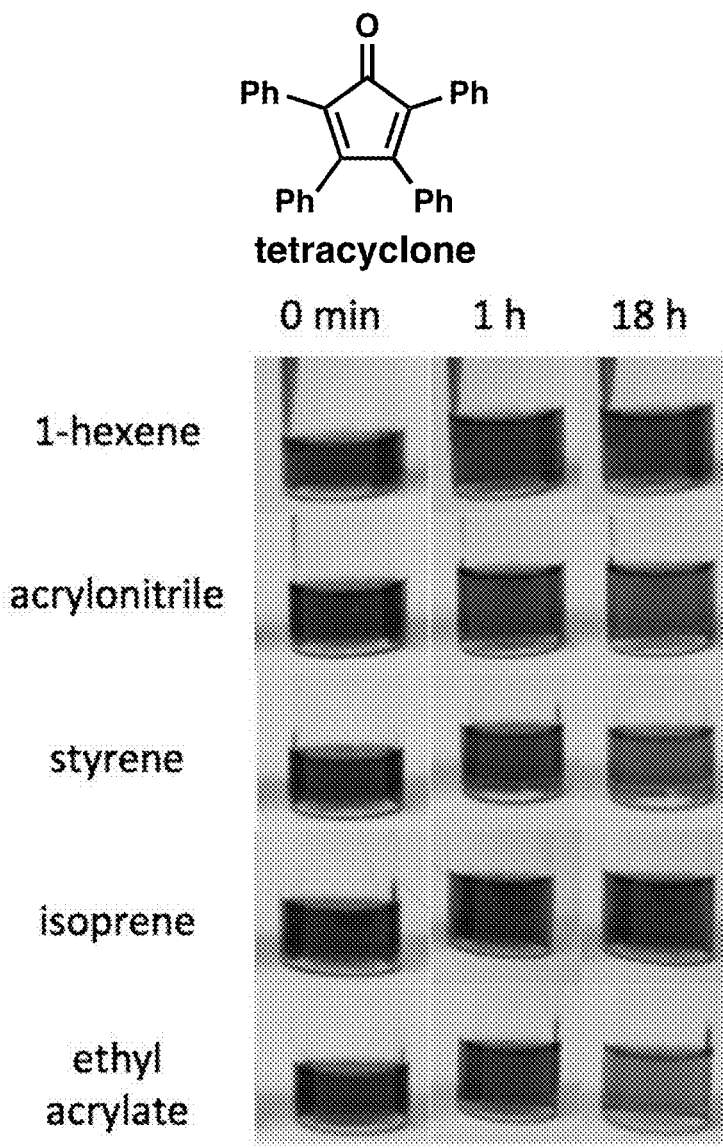
FIG. 19 shows photographs of a demonstration of selective electron-poor alkene detection.

FIG. 19 is a demonstration of selective electron-poor alkene detection. To tetraphenylcyclopentadienone (tetracyclone) (1 mM) dissolved in chloroform was added alkene (molar excess). Experiments were conducted under ambient atmosphere and temperature. Results were observed and recorded with a digital camera after 0, 1, and 18 hours of reaction. Electron-poor alkenes (acrylonitrile, ethyl acrylate) reacted after 18 hours with tetracyclone. Electron-rich alkenes (1-hexene, isoprene, styrene) reacted slowly or not at all.

Figure 20:
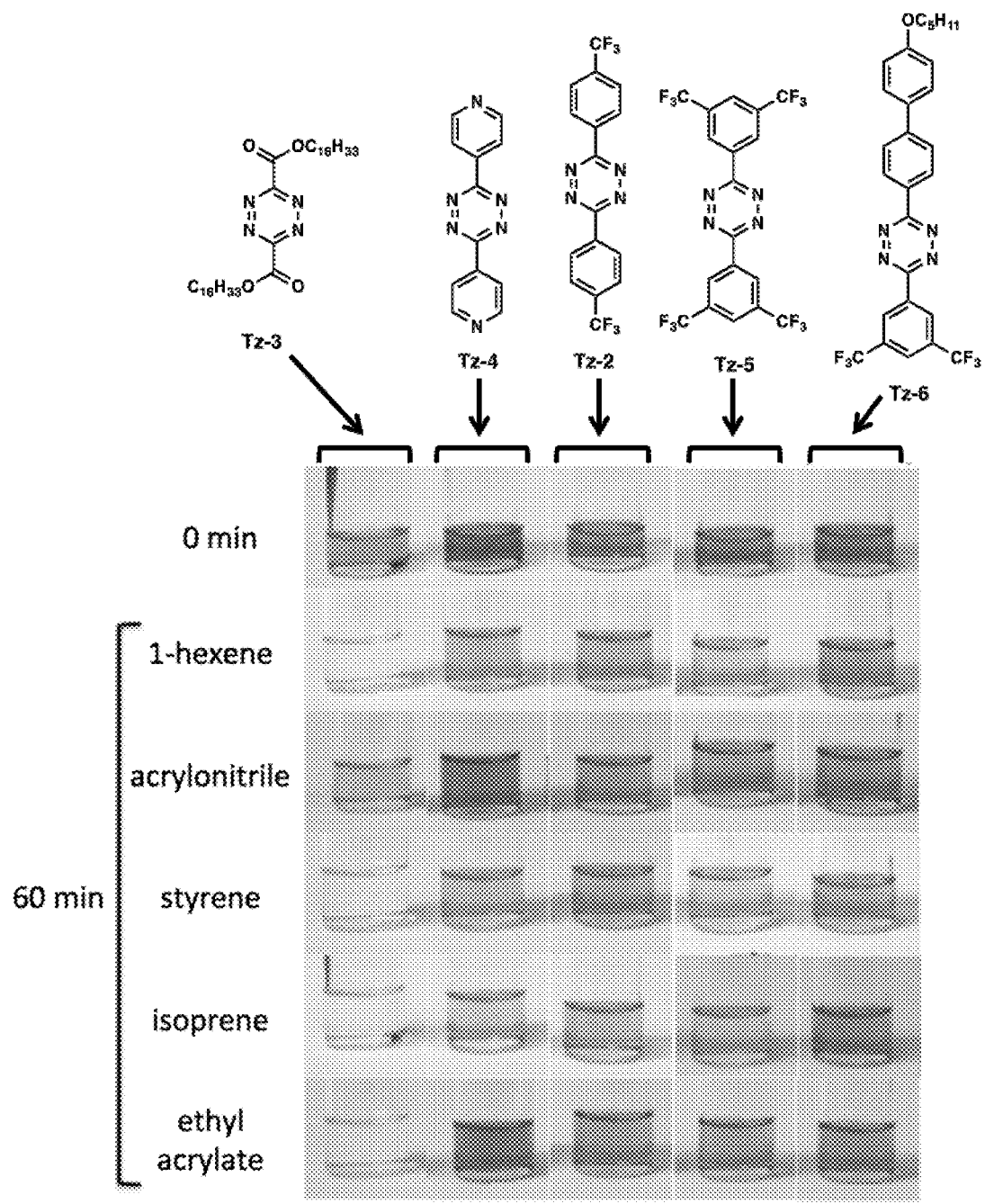
FIG. 20 shows photographs of a demonstration of other tetrazines selectively reaction with electron rich alkenes.

FIG. 20 is a demonstration of other tetrazines selectively reaction with electron rich alkenes. To tetrazines (Tz-2-Tz-6) (1 mM) dissolved in chloroform was added alkene (molar excess). Experiments were conducted under ambient atmosphere and temperature. Results were observed and recorded with a digital camera after 0 and 60 minutes of reaction. All tested alkenes reacted with Tz-3, although acrylonitrile reacted the slowest. Electron-rich alkenes (1-hexene, isoprene, styrene) reacted with slowly with Tz-4. Electron-poor alkenes (acrylonitrile, ethyl acrylate) reacted very slowly or not at all with Tz-4. Electron-rich alkenes (1-hexene, isoprene, styrene) reacted slowly with Tz-2. Electron-poor alkenes (acrylonitrile, ethyl acrylate) reacted very slowly or not at all with Tz-2. Electron-rich alkenes (1-hexene, isoprene, styrene) reacted slowly with Tz-5. Electron-poor alkenes (acrylonitrile, ethyl acrylate) reacted very slowly or not at all with Tz-5. Electron-rich alkenes (1-hexene, isoprene, styrene) reacted slowly with Tz-6. Electron-poor alkenes (acrylonitrile, ethyl acrylate) reacted very slowly or not at all with Tz-6.

Figure 21:
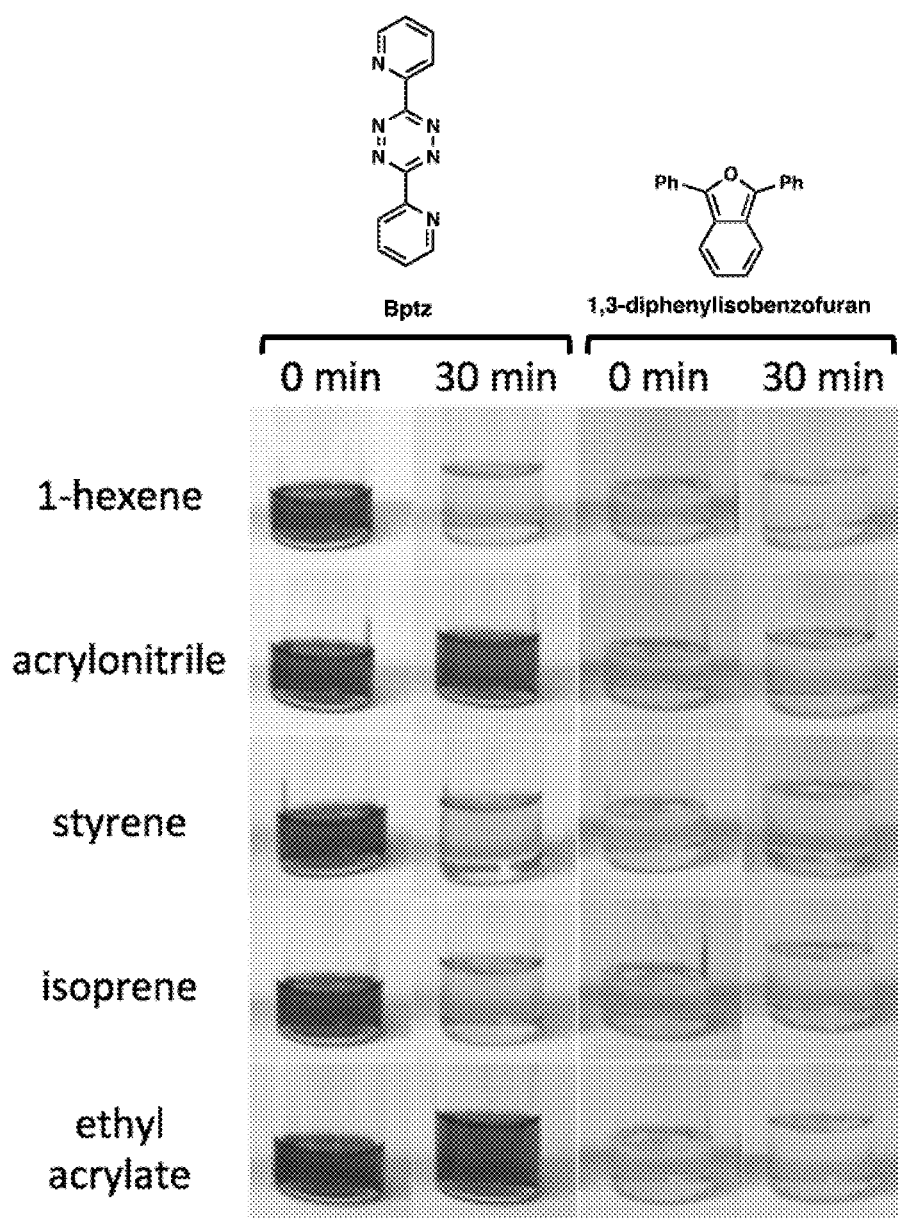
FIG. 21 shows photographs of a demonstration of complementary reactivity of Bptz and 1,3-diphenylisobenzofuran.

FIG. 21 is a demonstration of complementary reactivity of Bptz and 1,3-diphenylisobenzofuran. To Bptz dissolved in chloroform (5 mM) was added alkene (molar excess). To 1,3-diphenylisobenzofuran (1 mM) dissolved in chloroform was added alkene (molar excess). Experiments were conducted under ambient atmosphere and temperature. Results were observed and recorded with a digital camera after 0 and 30 minutes of reaction. Electron-poor alkenes (acrylonitrile, ethyl acrylate) reacted readily with 1,3-diphenylisobenzofuran with a concomitant loss of color. Electron-rich alkenes (1-hexene, isoprene, styrene) reacted slowly or not at all with 1,3-diphenylisobenzofuran without a perceivable loss of color. Electron-rich alkenes (1-hexene, isoprene, styrene) reacted readily with Bptz with a concomitant change in color. Electron-poor alkenes (acrylonitrile, ethyl acrylate) reacted slowly or not at all with Bptz with little or no perceivable change in color.

Other embodiments are within the scope of the following claims.

What is claimed is:

1. A detector for detecting an analyte comprising:
   a housing including a detection region having a machine readable pattern, the housing comprising
   a compound having an extrudable group and capable of undergoing Diels-Alder reaction with the analyte including a carbon-carbon multiple bond moiety and
   a conducting material including the compound that changes conductivity after the Diels-Alder reaction, the detector including a metal salt.

2. The detector of claim 1, wherein the analyte includes ethylene.

3. The detector of claim 1, wherein the compound includes a heteroaromatic compound.

4. The detector of claim 1, wherein the heteroaromatic compound includes a tetrazine.

5. The detector of claim 1, wherein the extrudable group includes a di-nitrogen group.

6. The detector of claim 1, wherein the compound selectively reacts with a sterically unencumbered alkene.

7. The detector of claim 1, wherein the compound selectively reacts with a sterically unencumbered alkyne.

8. The detector of claim 1, wherein the detection region includes a colorimetric indicator that changes color after the Diels-Alder reaction.

9. The detector of claim 1, wherein the detector includes one or more metal salts including a copper salt, a nickel salt, a silver salt, a zinc salt, an aluminum salt, a palladium salt, a platinum salt, a rhodium salt, a ruthenium salt, or a gold salt.

10. The detector of claim 1, wherein the detector includes a reader capable of reading the pattern.

11. The detector of claim 1, wherein the detector is a color based detector.

12. The detector of claim 1, wherein the detector is a fluorescence based detector.

13. The detector of claim 1, wherein the detector is resistivity based detector.

* * * * *